US010617755B2

(12) United States Patent
Bais et al.

(10) Patent No.: US 10,617,755 B2
(45) Date of Patent: Apr. 14, 2020

(54) COMBINATION THERAPY FOR THE TREATMENT OF GLIOBLASTOMA

(71) Applicant: Genentech, Inc., South San Francisco, CA (US)

(72) Inventors: Carlos Bais, South San Francisco, CA (US); Richard Bourgon, South San Francisco, CA (US); Heidi Phillips, South San Francisco, CA (US); Thomas Sandmann, South San Francisco, CA (US)

(73) Assignee: Genentech, Inc., South San Francisco, CA (US)

(*) Notice: Subject to any disclaimer, the term of this patent is extended or adjusted under 35 U.S.C. 154(b) by 0 days.

(21) Appl. No.: 14/470,443

(22) Filed: Aug. 27, 2014

(65) Prior Publication Data
US 2015/0065781 A1 Mar. 5, 2015

Related U.S. Application Data

(60) Provisional application No. 62/004,687, filed on May 29, 2014, provisional application No. 61/872,165, filed on Aug. 30, 2013.

(51) Int. Cl.
A61K 39/395 (2006.01)
C07K 16/22 (2006.01)
A61K 31/495 (2006.01)
A61K 45/06 (2006.01)
A61K 39/00 (2006.01)

(52) U.S. Cl.
CPC ........ A61K 39/3955 (2013.01); A61K 31/495 (2013.01); A61K 39/39541 (2013.01); A61K 45/06 (2013.01); C07K 16/22 (2013.01); A61K 2039/505 (2013.01)

(58) Field of Classification Search
CPC ...... C07K 16/22; A61K 45/06; A61K 31/495; A61K 2039/505; A61K 2300/00; A61P 35/00
See application file for complete search history.

(56) References Cited

U.S. PATENT DOCUMENTS

| 5,500,362 | A | 3/1996 | Robinson et al. | |
|---|---|---|---|---|
| 6,054,297 | A | 4/2000 | Carter et al. | |
| 6,582,959 | B2 | 6/2003 | Kim | |
| 6,703,020 | B1 | 3/2004 | Thorpe et al. | |
| 6,884,879 | B1* | 4/2005 | Baca .................. | C07K 16/22 435/320.1 |
| 7,060,269 | B1 | 6/2006 | Baca et al. | |
| 2002/0032315 | A1 | 3/2002 | Baca et al. | |
| 2003/0190317 | A1 | 10/2003 | Baca et al. | |
| 2003/0203409 | A1 | 10/2003 | Kim | |
| 2003/0206899 | A1 | 11/2003 | Ferrara et al. | |
| 2005/0186208 | A1 | 8/2005 | Fyfe et al. | |
| 2006/0009360 | A1 | 1/2006 | Pifer et al. | |
| 2007/0141066 | A1* | 6/2007 | Phillips .................. | A61K 45/06 424/155.1 |
| 2010/0226880 | A1 | 9/2010 | Fyfe et al. | |
| 2010/0266589 | A1 | 10/2010 | Hedrick et al. | |
| 2011/0206662 | A1 | 8/2011 | Dupont et al. | |
| 2013/0216533 | A1† | 8/2013 | Bais | |
| 2014/0342924 | A1 | 11/2014 | Harkin et al. | |
| 2015/0056190 | A1 | 2/2015 | Hegde et al. | |
| 2015/0064178 | A1 | 3/2015 | Bais et al. | |
| 2015/0148585 | A1 | 5/2015 | Das et al. | |
| 2016/0002732 | A1 | 1/2016 | Harkin et al. | |
| 2017/0051360 | A1 | 2/2017 | Bais et al. | |

FOREIGN PATENT DOCUMENTS

| CN | 102575298 A | 7/2012 |
|---|---|---|
| EP | 0666868 B1 | 4/2002 |
| EP | 3038647 B1 | 3/2019 |
| JP | 2007-526897 A | 9/2007 |
| JP | 2013-520442 A | 6/2013 |
| JP | 2013-536240 A | 9/2013 |
| TW | 201138819 A1 | 11/2011 |
| WO | WO-89/06692 A1 | 7/1989 |
| WO | WO-94/10202 A1 | 5/1994 |
| WO | WO-95/27062 A1 | 10/1995 |
| WO | WO-96/30046 A1 | 10/1996 |
| WO | WO-98/45332 A2 | 10/1998 |
| WO | WO-2005/012359 A2 | 2/2005 |
| WO | WO-2005/016968 A2 | 2/2005 |
| WO | WO-2005/044853 A2 | 5/2005 |
| WO | WO-2007/111733 A2 | 10/2007 |
| WO | WO-2008/109423 A1 | 9/2008 |
| WO | WO-2011/020049 A1 | 2/2011 |
| WO | WO-2011/106300 A2 | 9/2011 |
| WO | WO-2012/027379 A2 | 3/2012 |
| WO | WO-2012/167278 A1 | 12/2012 |

(Continued)

OTHER PUBLICATIONS

Chinot et al., Adv Ther 28(4): 334-340, 2011.*
Yu et al., Investigative Ophthalmology & Visual Science 49(2): 522-527, Feb. 2008.*
Vrendenburgh et al., Int J Radiation Oncology Biol Phys 82(1): 58-66, 2012.*
Lloyd et al., Protein Engineering, Design & Selection 22:159-168 (Year: 2009).*
Edwards et al., J Mol Biol. 334(1): 103-118 (Year: 2003).*
Cooper et al., "The proneural molecular signature is enriched in oligodendrogliomas and predicts improved survival among diffuse gliomas," PLoS One. 5(9):e12548 (9 pages).
Lai et al., "Phase II study of bevacizumab plus temozolomide during and after radiation therapy for patients with newly diagnosed glioblastoma multiforme," J Clin Oncol. 29(2):142-8 (2011).

(Continued)

Primary Examiner — Phuong Huynh
(74) Attorney, Agent, or Firm — Clark & Elbing LLP; Karen L. Elbing

(57) ABSTRACT

This invention concerns methods of treating a patient diagnosed with glioblastoma comprising administering to said patient a therapy comprising an effective amount of an anti-VEGF antibody and a chemotherapeutic.

18 Claims, 8 Drawing Sheets

Specification includes a Sequence Listing.

(56) References Cited

FOREIGN PATENT DOCUMENTS

| WO | WO-2013/106765 A1 | 7/2013 |
|---|---|---|
| WO | WO-2013/148288 A1 | 10/2013 |
| WO | WO-2014/025813 A1 | 2/2014 |
| WO | WO-2014/087156 A1 | 6/2014 |
| WO | WO-2015/031782 A1 | 3/2015 |

OTHER PUBLICATIONS

Narayana et al., "A clinical trial of bevacizumab, temozolomide, and radiation for newly diagnosed glioblastoma," J Neurosurg. 116(2):341-5 (2012).
International Search Report and Written Opinion for International Patent Application No. PCT/US14/53463, dated Dec. 4, 2014 (18 pages).
International Preliminary Report on Patentability for International Patent Application No. PCT/US2014/053463, dated Mar. 1, 2016 (6 pages).
Carmeliet et al., "Angiogenesis in cancer and other diseases," Nature. 407(6801):249-57 (2000).
Chinot et al., "Bevacizumab plus radiotherapy-temozolomide for newly diagnosed glioblastoma," N Engl J Med. 370(8):709-22 (2014).
Cloughsey et al., "Phase III Trial of Bevacizumab Added to Standard Radiotherapy and Temozolomide for Newly Diagnosed Glioblastoma: Final Progression-Free Survival and Preliminary Overall Survival Results from AVAglio (PL02.002)," Neurology. 80(Meeting Abstracts 1):PL02.002 (2013) (2 pages).
Ferrara, "Vascular endothelial growth factor. The trigger for neovascularization in the eye," Lab Invest. 72(6):615-8 (1995).
Friedman et al., "Irinotecan therapy in adults with recurrent or progressive malignant glioma," J Clin Oncol. 17(5):1516-25 (1999).
Gossmann et al., "Dynamic contrast-enhanced magnetic resonance imaging as a surrogate marker of tumor response to anti-angiogenic therapy in a xenograft model of glioblastoma multiforme," J Magn Reson Imaging. 15(3):233-40 (2002).
Hasan et al., "VEGF antagonists," Expert Opin Biol Ther. 1(4):703-18 (2001).
Houck et al., "The vascular endothelial growth factor family: identification of a fourth molecular species and characterization of alternative splicing of RNA," Mol Endocrinol. 5(12):1806-14 (1991).
Leung et al., "Vascular endothelial growth factor is a secreted angiogenic mitogen," Science. 246(4935):1306-9 (1989).
Macdonald et al., "Response criteria for phase II studies of supratentorial malignant glioma," J Clin Oncol. 8(7):1277-80 (1990).
Matthews et al., "A receptor tyrosine kinase cDNA isolated from a population of enriched primitive hematopoietic cells and exhibiting close genetic linkage to c-kit," Proc Natl Acad Sci U S A. 88(20):9026-30 (1991).
Meyer et al., "A novel vascular endothelial growth factor encoded by Orf virus, VEGF-E, mediates angiogenesis via signalling through VEGFR-2 (KDR) but not VEGFR-1 (Flt-1) receptor tyrosine kinases," EMBO J. 18(2):363-74 (1999).
Muller et al., "VEGF and the Fab fragment of a humanized neutralizing antibody: crystal structure of the complex at 2.4 Å resolution and mutational analysis of the interface," Structure. 6(9):1153-67 (1998).
Ogawa et al., "A novel type of vascular endothelial growth factor, VEGF-E (NZ-7 VEGF), preferentially utilizes KDR/Flk-1 receptor and carries a potent mitotic activity without heparin-binding domain," J Biol Chem. 273(47):31273-82 (1998).
Oken et al., "Toxicity and response criteria of the Eastern Cooperative Oncology Group," Am J Clin Oncol. 5(6):649-55 (1982).
Popkov et al., "Human/mouse cross-reactive anti-VEGF receptor 2 recombinant antibodies selected from an immune b9 allotype rabbit antibody library," J Immunol Methods. 288(1-2):149-64 (2004).
Presta et al., "Humanization of an anti-vascular endothelial growth factor monoclonal antibody for the therapy of solid tumors and other disorders," Cancer Res. 57(20):4593-9 (1997).
Schlessinger et al., "Growth factor signaling by receptor tyrosine kinases," Neuron. 9(3):383-91 (1992).
Stupp et al., "Radiotherapy plus concomitant and adjuvant temozolomide for glioblastoma," N Engl J Med. 352(10):987-96 (2005).
Taphoorn et al., "Health-Related Quality of Life in a Randomized Phase III Study of Bevacizumab, Temozolomide, and Radiotherapy in Newly Diagnosed Glioblastoma," J Clin Oncol. 33(19):2166-75 (2015) (14 pages).
Terman et al., "Identification of a new endothelial cell growth factor receptor tyrosine kinase," Oncogene. 6(9):1677-83 (1991).
Ullrich et al., "Signal transduction by receptors with tyrosine kinase activity," Cell. 61(2):203-12 (1990).
Wick et al., "Chemotherapie bei Gliomen," Onkologe. 17:44-54 (2011) (English language abstract).
Yarden et al., "Growth factor receptor tyrosine kinases," Annu Rev Biochem. 57:443-78 (1988).
International Preliminary Report on Patentability for International Patent Application No. PCT/US2013/053841, dated Feb. 10, 2015 (6 pages).
International Preliminary Report on Patentability for International Patent Application No. PCT/US2014/053500, dated Mar. 1, 2016 (14 pages).
International Search Report and Written Opinion for International Patent Application No. PCT/US2013/053841, dated Oct. 25, 2013 (10 pages).
International Search Report and Written Opinion for International Patent Application No. PCT/US2014/053500, dated Feb. 23, 2015 (19 pages).
Office Action for U.S. Appl. No. 11/763,288, dated Apr. 16, 2009 (14 pages).
"Avastin Improves the Quality of Life of Patients Having the Most Aggressive Form of Brain Tumor," Roche Press Release, published Sep. 30, 2009, retrieved from <http://www.roche.ru/home/prjess-zjentr/news/news-2009-09-30.html> Sep. 8, 2017 (9 pages).
"Discussion: Recent Developments in Giloblastoma Treatment—The Impact of AVAglio Trials on Clinical Practice," Nikkei Medical Online Cancer Experts, retrieved from <http://medical.nikkeibp.co.jp/all/data/cancerex/ar_rd_gbm201303.pdf> on Jun. 16, 2017 (partial English translation included) (16 pages).
"Glioma—From Examination to Diagnosis, Treatment, and Follow-Up—Treatment for Cerebral Edema," Center for Cancer Control and Information Services, National Cancer Center, published Jul. 2012, retrieved from <http://ganjoho.jp/data/public/qa_links/brochure/odjrh3000000ul06-att/118.pdf> on Aug. 8, 2017 (partial English translation included) (29 pages).
"Recent Developments in Giloblastoma Treatment—The Impact of AVAglio Trials on Clinical Practice," Nikkei Medical Oncology, published Apr. 24, 2013, retrieved from <http://medical.nikkeibp.co.jp/inc/all/search/cancer/report/> (partial English translation included) (25 pages).
DeLay et al., "Microarray analysis verifies two distinct phenotypes of glioblastomas resistant to antiangiogenic therapy," Clin Cancer Res. 18(10):2930-42 (2012).
Desjardins et al., "Bevacizumab and daily temozolomide for recurrent glioblastoma," Cancer. 118(5):1302-12 (2012).
Gerstner et al., "Anti-vascular endothelial growth factor therapy for malignant glioma," available in PMC Mar. 14, 2016, published in final edited form as: Curr Neurol Neurosci Rep. 9(3):254-62 (2009) (15 pages).
Gruber et al., "Bevacizumab in combination with radiotherapy plus concomitant and adjuvant temozolomide for newly diagnosed glioblastoma: Update progression-free survival, overall survival, and toxicity," J Clin Oncol. 27:15s Abstract 2017 (2009).
Kilickap et al., "Complete remission after bevacizumab plus temozolomide in a patient with recurrent glioblastoma multiforme," Acta Oncol. 51(4):544-6 (2012) (4 pages).
Phillips et al., "Molecular subclasses of high-grade glioma predict prognosis, delineate a pattern of disease progression, and resemble stages in neurogenesis," Cancer Cell. 9(3):157-73 (2006).
Sathornsumetee et al., "Tumor angiogenic and hypoxic profiles predict radiographic response and survival in malignant astrocytoma patients treated with bevacizumab and irinotecan," J Clin Oncol. 26(2):271-8 (2008).

(56) References Cited

OTHER PUBLICATIONS

Sulman et al., "Molecular predictors of outcome and response to bevacizumab (BEV) based on analysis of RTOG 0825, a phase III trial comparing chemoradiation (CRT) with and without BEV in patients with newly diagnosed glioblastoma (GBM)," J Clin Oncol. 31(suppl): abstract LBA2010 (2013) (2 pages).
Verhaak et al., "Integrated genomic analysis identifies clinically relevant subtypes of glioblastoma characterized by abnormalities in PDGFRA, IDH1, EGFR, and NF1," Cancer Cell. 17(1):98-110 (2010).
Communication pursuant to Rule 164(1) for European Patent Application No. 14839805.0, dated Feb. 17, 2017 (6 pages).
Extended European Search Report for European Patent Application No. 14839805.0, dated Jun. 14, 2017 (12 pages).
Extended European Search Report for European Patent Application No. 14840968.3, dated Mar. 14, 2017 (8 pages).
Office Action for U.S. Appl. No. 14/616,505, dated Mar. 8, 2017 (27 pages).
Search Report for Singaporean Patent Application No. 11201601471S, dated Feb. 7, 2017 (4 pages).
Written Opinion for Singaporean Patent Application No. 11201601404V, dated Dec. 15, 2016 (7 pages).
Written Opinion for Singaporean Patent Application No. 11201601471S, dated Mar. 3, 2017 (9 pages).
Avastin Product Label.
Avastin Product Label and Full Prescribing Information, amended Jun. 2006 (36 pages).
Avastin Product Label and Full Prescribing Information, amended May 2012 (28 pages).
Temodar Product Label and Full Prescribing Information, amended Mar. 2005 (31 pages).
Fiebig et al., "Do gene signatures predict effectiveness of bevacizumab and cetuximab?" J Clin Oncol. 26(15_suppl):14519 (2008).
Nagpal et al., "Bevacizumab improves quality of life in patients with recurrent glioblastoma," Chemother Res Pract. 2011: 602812 (2011) (6 pages).
Piao et al., "Acquired resistance to anti-VEGF therapy in glioblastoma is associated with a mesenchymal transition," Clin Cancer Res. 19(16):4392-403 (2013).
Sandmann et al., "Patients With Proneural Glioblastoma May Derive Overall Survival Benefit From the Addition of Bevacizumab to First-Line Radiotherapy and Temozolomide: Retrospective Analysis of the AVAglio Trial," J Clin Oncol. 33(25):2735-44 (2015) (12 pages).
Schneider et al. "Gliomas in adults," Dtsch Arztebl Int. 107(45):799-808 (2010) (11 pages).
West et al., "JAMA Oncology Patient Page. Performance Status in Patients with Cancer," JAMA Oncol. 1(7):998 (2015).
Yang et al., "Gene expression profile and angiogenic markers correlate with response to neoadjuvant bevacizumab followed by bevacizumab plus chemotherapy in breast cancer," Clin Cancer Res. 14(18):5893-9 (2008).
Communication pursuant to Article 94(3) for European Patent Application No. 14839805.0, dated Jan. 16, 2018 (4 pages).
International Preliminary Report on Patentability for International Patent Application No. PCT/US2015/040408, dated Jan. 17, 2017 (11 pages).
International Search Report and Written Opinion for International Patent Application No. PCT/US2015/040408, dated Dec. 21, 2015 (19 pages).
Invitation to Pay Additional Fees for International Application No. PCT/US2015/040408, dated Oct. 15, 2015 (8 pages).

Office Action for U.S. Appl. No. 14/471,734, dated Jan. 10, 2018 (12 pages).
Office Action for U.S. Appl. No. 14/616,505, dated Nov. 3, 2017 (13 pages).
Office Action for U.S. Appl. No. 15/346,164, dated Mar. 9, 2018 (11 pages).
Huse et al., "Survival benefit from bevacizumab in newly diagnosed glioblastoma (GBM) according to transcriptional subclasses." J Clin Oncol Suppl. 31(15):2057 (2013).
Notice of Reasons for Rejection for Japanese Patent Application No. 2016-537902, dated Aug. 21, 2018 (9 pages).
Decision of Rejection for Japanese Patent Application No. 2016-537902, dated Jul. 9, 2019 (4 pages).
English Translation of Office Action for Chinese Patent Application No. 201480053411.5, dated Dec. 3, 2018 (6 pages).
Examination Report for Australian Patent Application No. 2014312130, dated Jan. 23, 2019 (4 pages).
Notification of Defects in Israeli Patent Application No. 244014, dated Dec. 17, 2018 (8 pages).
Substantive Examination for Malaysian Patent Application No. PI 2016000369, dated Jan. 24, 2019 (4 pages).
AVASTIN® Product Label and Full Perscribing Information, revised May 2009 (22 pages).
Chinot et al., "Upfront bevacizumab may extend survival for glioblastoma patients who do not receive second-line therapy: an exploratory analysis of AVAglio," Neuro Oncol. 18(9):1313-8 (2016).
Dunn et al., "Emerging insights into th emolecular and cellular basis of glioblastoma," Genes and Development 26:756-84 (2012).
Friedman et al., "Bevacizumab alone and in combination with irinotecan in recurrent glioblastoma," J Clin Oncol. 27(28):4733-40 (2009).
Gerok et al., Chapter 15: Internistische Onkologie, *Die Innere Medizin*, Schattauer Verlagsgesellschaft mbH, IV, 1252 (2000) (4 pages) (English translation included).
Guareschi et al., "Glioblastoma multiforme: a review on causes, mechanisms, and solutions," Stem Cells Regen Med 3(1):1-6 (2019).
Ho et al., "Chemoirradiation for glipblastoma multiforme: the national cancer institute experience," PLoS One. 8(8):e70745 (2013) (8 pages).
Lai et al., "Phase II study of bevacizumab plus temozolomide during and after radiation therapy for patients with newly diagnosed glioblastoma multiforme," J Clin Oncol. 29(2):142-8 (2011) (Appendix Figure A1) (1 page).
Lee et al., "Anti-Vascular endothelial growth factor treatment augments tumor radiation response under normoxic or hypoxic conditions," Cancer Res. 60(19):5565-70 (2000).
Louis et al., "The 2007 WHO classification of tumors of the central nervous system," Acta Neuropathol. 114(2):97-109 (2007).
Mathieu et al., "Combining bevacizumab with temozolomide increases the antitumor efficacy of temozolomide in a human glioblastoma orthotopic xenograft model," Neoplasia. 10(12):1383-92 (2008).
Radiation Therapy Oncology Group (ROTG), Trial No. NCT00884741, 2009, Tabular View and Study Details (20 pages).
Scientific Discussion of Avastin, "Extension of the indication to include Avastin in combination with paclitaxel for the first-line treatment of patients with metastic breast cancer," London (2007) (13 pages).
TEMODAR® Product Label and Full Perscribing Information, revised Feb. 2011 (20 pages).
Zwiener et al., "Survival Analysis: Part 15 of a Series on Evaluation of Scientific Publications," Dtsch Arztebl Int. 108(10):163-9 (2011) (7 pages).

\* cited by examiner
† cited by third party

COMBINATION THERAPY FOR THE TREATMENT OF GLIOBLASTOMA

FIELD OF THE INVENTION

This invention concerns in general treatment of diseases and pathological conditions with anti-VEGF antibodies. More specifically, the invention concerns the treatment of human patients susceptible to or diagnosed with glioblastoma using an anti-VEGF antibody, in combination with one or more additional anti-tumor therapeutic agents.

BACKGROUND OF THE INVENTION

Gliomas account for 81% of all malignant brain and CNS tumors. Glioblastoma (glioblastoma multiforme (GBM); World Health Organization (WHO) grade IV astrocytoma), in particular, accounts for 60% to 70% of malignant gliomas and remains the most aggressive subtype of glioma. It occurs mostly in adults (median age at diagnosis: 64 years) and its incidence is estimated to be 3.05/100,000 in the United States. With 1- and 5-year overall survival of 29% and 3%, respectively, the prognosis of glioblastoma remains particularly poor (Central Brain Tumor Registry of the United States (2005) (CBTRUS; http://www.cbtrus.org)).

Although some progress has been made in the treatment of glioblastoma, this disease presents a highly unmet medical need with limited treatment options. In particular, bevacizumab (Avastin®), a monoclonal antibody targeted against the pro-angiogenic vascular endothelial growth factor (VEGF), holds significant therapeutic potential.

SUMMARY OF THE INVENTION

The present invention provides methods and kits for treating patients diagnosed with glioblastoma, including patients newly diagnosed with glioblastoma.

In one aspect, the invention provides methods of treating a patient diagnosed with a glioblastoma, including administering to the patient a therapy including an effective amount of an anti-VEGF antibody, an effective amount of a chemotherapeutic, and an effective amount of radiotherapy, wherein the treatment prolongs the patient's median overall survival (OS) time as compared to a glioblastoma patient receiving the chemotherapeutic without an anti-VEGF antibody.

In some embodiments, the patient can have a WHO performance status of ≤2. In some embodiments, the chemotherapeutic can be temozolomide (TMZ). In some embodiments, the effective amount of the TMZ can be 150 mg/m$^2$, optionally, administered orally. In some embodiments, the effective amount of the TMZ can be 200 mg/m$^2$, optionally, administered orally. In some embodiments, the radiotherapy can be administered at 2 Gy. In some embodiments, the anti-VEGF antibody can bind the A4.6.1 epitope. In some embodiments, the anti-VEGF antibody can be bevacizumab. In some embodiments, the anti-VEGF antibody may comprise a variable heavy chain (VH) and a variable light chain (VL), wherein the VH can have an amino acid sequence of EVQLVESGGGLVQPGGSLRLS-CAASGYTFTNYGMNWVRQAPGKGLEWVGWINTYT-GEPTYAADFKRR FTFSLDTSKSTAYLQMNSLRAED-TAVYYCAKYPHYYGSSHWYFDVWGQGTLVTVSS (SEQ ID NO: 2) and the VL can have an amino acid sequence of DIQMTQSPSS LSASVGDRVT ITCSASQDIS NYLNWYQQKPGKAPKVLIYFTSSLHSGVPSRFSGS-GSGTDFTLTISSLQPEDFATYYCQQYSTVPWTFG QGTKVEIKR (SEQ ID NO: 1). In some embodiments, the effective amount of the anti-VEGF antibody can be about 10 mg/kg (e.g., 10 mg/kg), optionally administered intravenously every two weeks, and can be, for example, administered initially intravenously over 90 minutes, with subsequent infusions over 60 minutes and then 30 minutes. In some embodiments, the effective amount of the anti-VEGF antibody can be about 15 mg/kg (e.g., 15 mg/kg), optionally administered intravenously every two weeks, and can be, for example, administered initially intravenously over 90 minutes, with subsequent infusions over 60 minutes and then 30 minutes. In some embodiments, the anti-VEGF antibody can be administered first to the patient at the first cycle, and, optionally, any subsequent administrations of the anti-VEGF antibody can be either prior to or after the chemotherapeutic. In another embodiment, the anti-VEGF antibody can be administered concurrently with the chemotherapeutic, and, optionally, radiotherapy. In some embodiments, administration of steroids to the patient can be discontinued. In some embodiments, the glioblastoma is of a proneural subtype. In some embodiments, the glioblastoma is a newly diagnosed glioblastoma.

In the methods described above, the median OS time may be prolonged by about 4.9 months with a hazard ratio (HR) equal to about 0.42, as compared to a glioblastoma patient receiving the chemotherapeutic without the anti-VEGF antibody. In another embodiment, the median OS time may be prolonged by about 4.9 months with a HR from about 0.24 to about 0.72, as compared to a glioblastoma patient receiving the chemotherapeutic without the anti-VEGF antibody. In another embodiment, the median OS time may be prolonged by at least 5 months or greater with a HR from about 0.24 to about 0.72, as compared to a glioblastoma patient receiving the chemotherapeutic without the anti-VEGF antibody. In some embodiments of the methods described above, the patient can be less than 65 years old. In other embodiments of the methods described above, the patient can be equal to or greater than 65 years old.

In another aspect, the invention provides kits including an anti-VEGF antibody binding essentially to epitope A4.6.1, a chemotherapeutic, and a package insert or label with instructions to treat a patient diagnosed with a glioblastoma, including administering to the patient an effective amount of an anti-VEGF antibody and a chemotherapeutic, wherein the treatment prolongs the patient's median OS time as compared to a glioblastoma patient receiving the chemotherapeutic without the anti-VEGF antibody. In some embodiments of this aspect, the patient may have received two or fewer prior anti-cancer regimens. In some embodiments of this aspect, the anti-VEGF antibody can be bevacizumab. In some embodiments of this aspect, the glioblastoma is of a proneural subtype. In some embodiments of this aspect, the glioblastoma is a newly diagnosed glioblastoma.

BRIEF DESCRIPTION OF THE DRAWINGS

FIG. 3 is a summary based on the same multivariate analyses shown in FIGS. 4A and 4B.

DETAILED DESCRIPTION OF EMBODIMENTS OF THE INVENTION

I. Definitions

Figure 1:
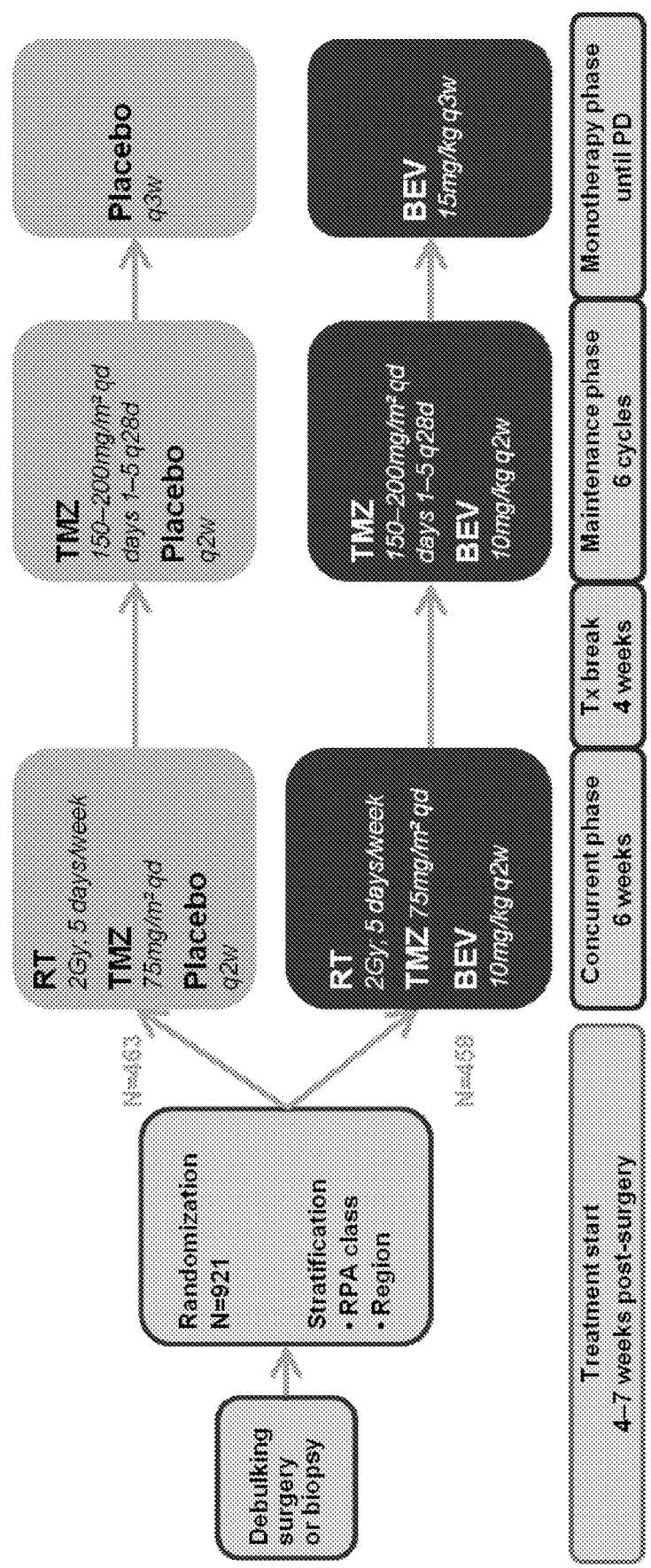
FIG. 1 is a diagram showing the two-arm Phase III study design treatment sequence as disclosed in more detail in Example 1. Study treatment started between 4 and 7 weeks after debulking surgery or biopsy of the glioblastoma and included 3 different phases: a concurrent phase during which 10 mg/kg bevacizumab or placebo was administered every two weeks in combination with temozolomide (TMZ) and radiotherapy followed by a treatment break of 28 days; a maintenance phase during which 10 mg/kg bevacizumab or placebo was administered every two weeks in combination with TMZ; and a monotherapy phase during which 15 mg/kg bevacizumab or placebo was administered every three weeks until disease progression.

An "anti-angiogenesis agent" or "angiogenesis inhibitor" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent as defined throughout the specification or known in the art, e.g., but are not limited to, antibodies to VEGF-A or to the VEGF-A receptor (e.g., KDR receptor or Flt-1 receptor), VEGF-trap, anti-PDGFR inhibitors such as Gleevec™ (Imatinib Mesylate). Anti-angiogensis agents also include native angiogenesis inhibitors, e.g., angiostatin, endostatin, etc. See, e.g., Klagsbrun and D'Amore, Annu. Rev. Physiol., 53:217-39 (1991); Streit and Detmar, Oncogene, 22:3172-3179 (2003) (e.g., Table 3 listing anti-angiogenic therapy in malignant melanoma); Ferrara & Alitalo, Nature Medicine 5:1359-1364 (1999); Tonini et al., Oncogene, 22:6549-6556 (2003) (e.g., Table 2 listing known antiangiogenic factors); and Sato. Int. J. Clin. Oncol., 8:200-206 (2003) (e.g., Table 1 lists anti-angiogenic agents used in clinical trials).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The term "VEGF" or "VEGF-A" is used to refer to the 165-amino acid human vascular endothelial cell growth factor and related 121-, 145-, 189-, and 206-amino acid human vascular endothelial cell growth factors, as described by, e.g., Leung et al. Science, 246:1306 (1989), and Houck et al. Mol. Endocrin., 5:1806 (1991), together with the naturally occurring allelic and processed forms thereof. VEGF-A is part of a gene family including VEGF-B, VEGF-C, VEGF-D, VEGF-E, VEGF-F, and PlGF. VEGF-A primarily binds to two high affinity receptor tyrosine kinases, VEGFR-1 (Flt-1) and VEGFR-2 (Flk-1/KDR), the latter being the major transmitter of vascular endothelial cell mitogenic signals of VEGF-A. Additionally, neuropilin-1 has been identified as a receptor for heparin-binding VEGF-A isoforms, and may play a role in vascular development. The term "VEGF" or "VEGF-A" also refers to VEGFs from non-human species such as mouse, rat, or primate. Sometimes the VEGF from a specific species is indicated by terms such as hVEGF for human VEGF or mVEGF for murine VEGF. Typically, VEGF refers to human VEGF. The term "VEGF" is also used to refer to truncated forms or fragments of the polypeptide comprising amino acids 8 to 109 or 1 to 109 of the 165-amino acid human vascular endothelial cell growth factor. Reference to any such forms of VEGF may be identified in the application, e.g., by "VEGF (8-109)," "VEGF (1-109)" or "VEGF165." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF.

An "anti-VEGF antibody" is an antibody that binds to VEGF with sufficient affinity and specificity. The antibody selected will normally have a binding affinity for VEGF, for example, the antibody may bind hVEGF with a Kd value of between 100 nM-1 pM. Antibody affinities may be determined by a surface plasmon resonance based assay (such as the BIAcore assay as described in PCT Application Publication No. WO2005/012359); enzyme-linked immunoabsorbent assay (ELISA); and competition assays (e.g. RIA's), for example. In certain embodiments, the anti-VEGF antibody of the invention can be used as a therapeutic agent in targeting and interfering with diseases or conditions wherein the VEGF activity is involved. Also, the antibody may be subjected to other biological activity assays, e.g., in order to evaluate its effectiveness as a therapeutic. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). An anti-VEGF antibody will usually not bind to other VEGF homologues such as VEGF-B or VEGF-C, nor other growth factors such as PlGF, PDGF or bFGF.

The anti-VEGF antibody "Bevacizumab (BV or Bev)," also known as "rhuMAb VEGF," or "Avastin®", is a recombinant humanized anti-VEGF monoclonal antibody generated according to Presta et al., *Cancer Res.* 57:4593-4599 (1997). It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of Bevacizumab, including most of the framework regions, is derived from human IgG1, and about 7% of the sequence is derived from the murine antibody A4.6.1. Bevacizumab has a molecular mass of about 149,000 Daltons and is glycosylated. Other anti-VEGF antibodies include the antibodies described in U.S. Pat. No. 6,884,879 and WO 2005/044853.

The "epitope A4.6.1" refers to the epitope recognized by the anti-VEGF antibody bevacizumab (AVASTIN®) (see Muller et al. *Structure.* 6: 1153-1167, 1998). In certain embodiments of the invention, the anti-VEGF antibodies include, but are not limited to, a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al. (*Cancer Res.* 57: 4593-4599, 1997).

A "functional epitope" according to this invention refers to amino acid residues of an antigen that contribute energetically to the binding of an antibody. Mutation of any one of the energetically contributing residues of the antigen (for example, mutation of wild-type VEGF by alanine or homolog mutation) will disrupt the binding of the antibody such that the relative affinity ratio (IC50mutant VEGF/IC50wild-type VEGF) of the antibody will be greater than 5 (see Example 2 of WO2005/012359). In one embodiment, the relative affinity ratio is determined by a solution binding phage displaying ELISA. Briefly, 96-well Maxisorp immunoplates (NUNC) are coated overnight at 4° C. with an Fab form of the antibody to be tested at a concentration of 2 µg/ml in PBS, and blocked with PBS, 0.5% BSA, and 0.05% Tween20 (PBT) for 2 h at room temperature. Serial dilutions of phage displaying hVEGF alanine point mutants (residues 8-109 form) or wild type hVEGF (8-109) in PBT are first incubated on the Fab-coated plates for 15 min at room temperature, and the plates are washed with PBS, 0.05% Tween20 (PBST). The bound phage is detected with an anti-M13 monoclonal antibody horseradish peroxidase (Amersham Pharmacia) conjugate diluted 1:5000 in PBT, developed with 3,3',5,5'-tetramethylbenzidine (TMB, Kirkegaard & Perry Labs, Gaithersburg, Md.) substrate for approximately 5 min, quenched with 1.0 M H3PO4, and read spectrophotometrically at 450 nm. The ratio of IC50 values (IC50, ala/IC50, wt) represents the fold of reduction in binding affinity (the relative binding affinity).

The anti-VEGF antibody Ranibizumab or the LUCENTIS® antibody or rhuFab V2 is a humanized, affinity-matured anti-human VEGF Fab fragment. Ranibizumab is produced by standard recombinant technology methods in *Escherichia coli* expression vector and bacterial fermentation. Ranibizumab is not glycosylated and has a molecular mass of ~48,000 daltons. See WO 98/45331 and US 2003/0190317.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light-chain and heavy chain variable domains.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al., *Cellular and Mol. Immunology*, 4th ed. (W. B. Saunders, Co., 2000). An antibody may be part of a larger fusion molecule, formed by covalent or non-covalent association of the antibody with one or more other proteins or peptides.

The terms "full-length antibody," "intact antibody," and "whole antibody" are used herein interchangeably to refer to an antibody in its substantially intact form, not antibody fragments as defined below. The terms particularly refer to an antibody with heavy chains that contain an Fc region.

"Antibody fragments" comprise a portion of an intact antibody, preferably comprising the antigen-binding region thereof. Examples of antibody fragments include Fab, Fab', F(ab')$_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields a F(ab')$_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody-hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of an antibody, wherein these domains are present in a single polypeptide chain. Generally, the scFv polypeptide further comprises a polypeptide linker between the VH and VL domains that enables the scFv to form the desired structure for antigen binding. For a review of scFv, see, e.g., Plückthün, in *The Pharmacology of Monoclonal Antibodies*, vol. 113, Rosenburg and Moore eds. (Springer-Verlag, New York: 1994), pp 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *PNAS USA* 90: 6444-6448 (1993). Triabodies and tetrabodies are also described in Hudson et al., *Nat. Med.* 9:129-134 (2003).

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target-binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal-antibody preparation is directed against a single determinant on an antigen. In addition to their specificity, monoclonal-antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., *Nature* 256:495-497 (1975); Hongo et al., *Hybridoma* 14 (3):253-260 (1995), Harlow et al., *Antibodies: A Laboratory Manual*, (Cold Spring Harbor Laboratory Press, 2$^{nd}$ ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature* 352:624-628 (1991); Marks et al., *J. Mol. Biol.* 222:581-597 (1992); Sidhu et al., *J. Mol. Biol.* 338(2):299-310 (2004); Lee et al., *J. Mol. Biol.*

340(5):1073-1093 (2004); Fellouse, *PNAS USA* 101(34): 12467-12472 (2004); and Lee et al., *J. Immunol. Methods* 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *PNAS USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10:779-783 (1992); Lonberg et al., *Nature* 368:856-859 (1994); Morrison, *Nature* 368:812-813 (1994); Fishwild et al., *Nature Biotechnol.* 14:845-851 (1996); Neuberger, *Nature Biotechnol.* 14:826 (1996); and Lonberg and Huszar, *Intern. Rev. Immunol.* 13:65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (e.g., U.S. Pat. No. 4,816,567 and Morrison et al., *PNAS USA* 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all, or substantially all, of the FRs are those of a human immunoglobulin sequence. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.* 227: 381 (1991); Marks et al., *J. Mol. Biol.* 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.* 147(1):86-95 (1991). See also van Dijk and van de Winkel, *Curr. Opin. Pharmacol.* 5:368-374 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *PNAS USA* 103: 3557-3562 (2006) regarding human antibodies generated via a human B-cell hybridoma technology.

The term "hypervariable region," "HVR," or "HV," when used herein refers to the regions of an antibody-variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993) and Sheriff et al., *Nature Struct. Biol.* 3:733-736 (1996).

A number of HVR delineations are in use and are encompassed herein. The HVRs that are Kabat complementarity-determining regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk, *J. Mol. Biol.* 196:901-917 (1987)). The AbM HVRs represent a compromise between the Kabat CDRs and Chothia structural loops, and are used by Oxford Molecular's AbM antibody-modeling software. The "contact" HVRs are based on an analysis of the available complex crystal structures. The residues from each of these HVRs are noted below.

| Loop | Kabat | AbM | Chothia | Contact | |
|---|---|---|---|---|---|
| L1 | L24-L34 | L24-L34 | L26-L32 | L30-L36 | |
| L2 | L50-L56 | L50-L56 | L50-L52 | L46-L55 | |
| L3 | L89-L97 | L89-L97 | L91-L96 | L89-L96 | |
| H1 | H31-H35B | H26-H35B | H26-H32 | H30-H35B | (Kabat Numbering) |
| H1 | H31-H35 | H26-H35 | H26-H32 | H30-H35 | (Chothia Numbering) |
| H2 | H50-H65 | H50-H58 | H53-H55 | H47-H58 | |
| H3 | H95-H102 | H95-H102 | H96-H101 | H93-H101 | |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (H2), and 93-102, 94-102, or 95-102 (H3) in the VH. The variable-domain residues are numbered according to Kabat et al., supra, for each of these extended-HVR definitions.

"Framework" or "FR" residues are those variable-domain residues other than the HVR residues as herein defined.

The expression "variable-domain residue-numbering as in Kabat" or "amino acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g., residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

An "affinity-matured" antibody is one with one or more alterations in one or more HVRs thereof which result in an improvement in the affinity of the antibody for antigen, compared to a parent antibody which does not possess those alteration(s). In one embodiment, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by VH- and VL-domain shuffling. Random mutagenesis of HVR and/or framework residues is described by, for example: Barbas et al., *Proc Nat. Acad. Sci. USA* 91:3809-3813 (1994); Schier et al., *Gene* 169:147-155 (1995); Yelton et al., *J. Immunol.* 155:1994-2004 (1995); Jackson et al., *J. Immunol.* 154(7):3310-3319 (1995); and Hawkins et al., *J. Mol. Biol.* 226:889-896 (1992).

The term "anti-neoplastic composition" or "anti-cancer composition" or "anti-cancer agent" refers to a composition useful in treating cancer comprising at least one active therapeutic agent, e.g., "anti-cancer agent." Examples of therapeutic agents (anti-cancer agents) include, but are limited to, e.g., chemotherapeutic agents, growth inhibitory agents, cytotoxic agents, agents used in radiation therapy, anti-angiogenesis agents, apoptotic agents, anti-tubulin agents, and other-agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (Tarceva™), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA VEGF, or VEGF receptor(s), TRAIL/Apo2, and other bioactive and organic chemical agents, etc. Combinations thereof are also included in the invention.

A "chemotherapeutic agent" or "chemotherapeutic" is a chemical compound useful in the treatment of cancer. Examples of chemotherapeutic agents include is a chemical compound useful in the treatment of cancer. Examples of chemotherapeutic agents include alkylating agents, such as, for example, temozolomide (TMZ), the imidazotetrazine derivative of the alkylating agent dacarbazine. Additional examples of chemotherapeutics agents include, e.g., paclitaxel or topotecan or pegylated liposomal doxorubicin (PLD). Other examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin; bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® docetaxel (Rhone- Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "growth inhibitory agent" when used herein refers to a compound or composition which inhibits growth and/or proliferation of a cell (e.g., a cell expressing Robo4) either in vitro or in vivo. Thus, the growth inhibitory agent may be one which significantly reduces the percentage of Robo4-expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as the anthracycline antibiotic doxorubicin ((8S-cis)-10-[(3-amino-2,3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione), epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The terms "sample" and "biological sample" are used interchangeably to refer to any biological sample obtained from an individual including body fluids, body tissue (e.g., tumor tissue), cells, or other sources. Body fluids are, e.g., lymph, sera, whole fresh blood, peripheral blood mononuclear cells, frozen whole blood, plasma (including fresh or frozen), urine, saliva, semen, synovial fluid and spinal fluid. Samples also include breast tissue, renal tissue, colonic tissue, brain tissue, muscle tissue, synovial tissue, skin, hair follicle, bone marrow, and tumor tissue. Methods for obtaining tissue biopsies and body fluids from mammals are well known in the art.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, increasing/extending overall survival (OS), increasing/extending progression-free survival (PFS), decreasing the rate of disease progression, amelioration or palliation of the disease state, and remission or improved prognosis.

By "monotherapy" is meant a therapeutic regimen that includes only a single therapeutic agent for the treatment of the cancer or tumor during the course of the treatment period. Monotherapy using a VEGF antagonist (e.g., an anti-VEGF antibody, e.g., bevacizumab) means that the VEGF antagonist is administered in the absence of an additional anti-cancer therapy during treatment period.

The term "effective amount" refers to an amount of a drug effective to treat a disease or disorder, such as glioblastoma, in a subject or patient, such as a mammal, e.g., a human. In the case of a cancer, such as glioblastoma, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer (e.g., glioblastoma). To the extent the drug may prevent growth and/or kill existing cancer cells, it may be cytostatic and/or cytotoxic. For cancer therapy, efficacy in vivo can, for example, be measured by assessing the duration of survival, duration of progression free survival (PFS), overall survival (OS), the response rates (RR), duration of response, and/or quality of life.

"Survival" refers to the subject remaining alive, and includes progression-free survival (PFS) and overall survival (OS). Survival can be estimated by the Kaplan-Meier method, and any differences in survival are computed using the stratified log-rank test.

"Overall survival" or "OS" refers to the subject remaining alive for a defined period of time, such as about 1 year, about 2 years, about 3 years, about 4 years, about 5 years, about 10 years, etc., from initiation of treatment or from initial diagnosis. In the studies underlying the present invention the event used for survival analysis was death from any cause.

"Progression-free survival" or "PFS" refers to the time from treatment (or randomization) to first disease progression or death. For example it is the time that the subject remains alive, without return of the cancer, e.g., for a defined period of time such as about 1 month, about 2 months, about 3 months, about 4, months, about 5 months, about 6 months, about 7 months, about 8 months, about 9 months, about 1 year, about 2 years, about 3 years, etc., from initiation of treatment or from initial diagnosis. In one aspect of the invention, PFS can be assessed by the MacDonald Response Criteria as described in MacDonald et al. (*J. Clin. Oncol.* 1990; 8: 1277-80, 1990).

"Overall response rate" or "Objective response rate" (ORR) refers to the percentage of people who experience a decrease in the size or amount of the cancer (e.g., the glioblastoma) for a minimum amount of time, and ORR can be represented by the sum of the complete and partial response rates.

By "extending survival" or "increasing the likelihood of survival" is meant increasing PFS and/or OS in a treated subject (e.g., a subject treated with an anti-VEGF antibody, e.g., bevacizumab) or population of treated subjects relative to an untreated subject (e.g., a subject not treated with an anti-VEGF antibody, e.g., bevacizumab) or population of untreated subjects, respectively, or relative to a control treatment protocol, such as treatment only with the chemotherapeutic agent, such as those uses in the standard of care for glioblastoma, such as, for example, temozolomide (TMZ) with or without radiotherapy. Survival is monitored for at least about one month, about two months, about four months, about six months, about nine months, or at least about 1 year, or at least about 2 years, or at least about 3 years, or at least about 4 years, or at least about 5 years, or at least about 10 years, etc., following the initiation of treatment or following the initial diagnosis.

Hazard ratio (HR) is a statistical definition for rates of events. For the purpose of the invention, hazard ratio is defined as representing the probability of an event in the experimental arm divided by the probability of an event in the control arm at any specific point in time. "Hazard ratio" in progression free survival analysis is a summary of the difference between two progression free survival curves, representing the reduction in the risk of death on treatment compared to control, over a period of follow-up.

A "patient" or "subject" herein refers to any single animal (including, for example, a mammal, such as a dog, a cat, a horse, a rabbit, a zoo animal, a cow, a pig, a sheep, a non-human primate, and a human), such as a human, eligible for treatment who is experiencing or has experienced one or more signs, symptoms, or other indicators of a disease or disorder, such as a glioblastoma (GBM). Intended to be included as a patient are any patients involved in clinical research trials not showing any clinical sign of disease, or patients involved in epidemiological studies, or patients once used as controls. The patient may have been previously treated with an anti-VEGF antibody, e.g., bevacizumab, or another drug, or not so treated. The patient may be naïve to an additional drug(s) being used when the treatment herein is started, i.e., the patient may not have been previously treated with, for example, a therapy other than an anti-VEGF antibody, e.g., bevacizumab, at "baseline" (i.e., at a set point in time before the administration of a first dose of an anti-VEGF antibody (e.g., bevacizumab) in the treatment method herein, such as the day of screening the subject before treatment is commenced). Such "naïve" patients or subjects are generally considered to be candidates for treatment with such additional drug(s).

The terms "cancer" and "cancerous" refer to or describe the physiological condition in mammals that is typically characterized by unregulated cell growth. Included in this definition are benign and malignant cancers as well as dormant tumors or micrometastatses. Examples of cancer include but are not limited to, carcinoma, lymphoma, blastoma, sarcoma, and leukemia. More particular examples of such cancers include, but are not limited to, glioblastoma (GBM), including, e.g., proneural GBM, neural GBM, classical GBM, and mesenchymal GBM. GBMs may be newly diagnosed, diagnosed, or recurrent. Other cancers include, for example, breast cancer, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, ovarian cancer, cervical cancer, liver cancer, bladder cancer, hepatoma, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

The term "pharmaceutical formulation" refers to a sterile preparation that is in such form as to permit the biological activity of the medicament to be effective, and which contains no additional components that are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

A "kit" is any manufacture (e.g., a package or container) comprising at least one reagent, e.g., a medicament for treatment of a patient having a glioblastoma or a probe for specifically detecting a biomarker gene or protein of the invention. The manufacture is preferably promoted, distributed, or sold as a unit for performing the methods of the present invention.

II. Therapeutic Uses and Compositions for the Treatment of Glioblastoma

The invention encompasses anti-angiogenic therapy, a cancer treatment strategy aimed at inhibiting the development of tumor blood vessels required for providing nutrients to support tumor growth. Because angiogenesis is involved in both primary tumor growth and metastasis, the anti-angiogenic treatment provided by the invention is capable of inhibiting the neoplastic growth of tumors at primary sites as well as preventing metastasis of tumors at secondary sites, therefore allowing attack of tumors by other therapeutics.

Specifically, provided herein are methods of treating a patient diagnosed with glioblastoma, comprising administering to the patient a treatment regimen combining an effective amount of a chemotherapeutic and an anti-VEGF antibody. The treatment regimen combining the chemotherapy and the administration of the anti-VEGF antibody extends the overall survival (OS) and/or the progression-free survival (PFS) of the subject.

A. Methods of Treatment

The present invention provides methods of treating a patient diagnosed with a glioblastoma, comprising administering to the patient a therapy including an effective amount of an anti-VEGF antibody (e.g., bevacizumab) and an effective amount of a chemotherapeutic (e.g., temozolomide (TMZ)). The subject may also be subjected to radiation therapy (radiotherapy). Such treatment can result in prolonged median OS time and/or PFS time of the treated patient as compared to that of a patient who received the same chemotherapeutic (e.g., TMZ) without an anti-VEGF antibody (e.g., bevacizumab).

The combination therapy may include one or more anti-VEGF antibodies (e.g., 1, 2, 3, 4, or 5 or more anti-VEGF antibodies) used in combination with one or more additional anti-cancer agents and/or therapies (e.g., 1, 2, 3, 4, or 5 or more additional anti-cancer agents and/or therapies). Examples of anti-cancer therapies include, without limitation, surgery, radiation therapy (radiotherapy), biotherapy, immunotherapy, chemotherapy (e.g., with the chemotherapeutic, TMZ), or a combination of these agents and/or therapies. In addition, cytotoxic agents, anti-angiogenic, and anti-proliferative agents can be used in combination with the anti-VEGF antibody (e.g., bevacizumab). The one or more additional anti-cancer agents or therapies preferably have complementary activities to the VEGF antagonist such that they do not adversely affect each other. The combined administration includes co-administration, using separate formulations or a single pharmaceutical formulation, and consecutive administration in either order, wherein preferably there is a time period while both (or all) active agents simultaneously exert their biological activities.

The one or more additional anti-cancer agent may be a chemotherapeutic agent, a cytotoxic agent, a cytokine, a growth inhibitory agent, an anti-hormonal agent, and combinations thereof. Such molecules are suitably present in combination in amounts that are effective for the purpose intended (i.e., treating a patient having a glioblastoma). For example, a pharmaceutical composition containing an anti-VEGF antibody (e.g., bevacizumab) may also comprise a therapeutically effective amount of an anti-neoplastic agent, a chemotherapeutic agent, a growth inhibitory agent, a cytotoxic agent, or combinations thereof.

Other therapeutic regimens in accordance with this invention may include administration of an anti-cancer agent and, including without limitation radiation therapy and/or bone marrow and peripheral blood transplants, and/or a cytotoxic agent, a chemotherapeutic agent, or a growth inhibitory agent. In one of such embodiments, a chemotherapeutic agent is an agent or a combination of agents such as, for example, cyclophosphamide, hydroxydaunorubicin, adriamycin, doxorubincin, vincristine (ONCOVIN™) prednisolone, CHOP, CVP, or COP, or immunotherapeutics such as anti-PSCA, anti-HER2 (e.g., HERCEPTIN®, OMNITARG™). In another embodiment, the combination includes docetaxel, doxorubicin, and cyclophosphamide. The combination therapy may be administered as a simultaneous or sequential regimen. When administered sequentially, the combination may be administered in two or more administrations. The combined administration includes co-administration, using separate formulations or a single pharmaceutical formulation, and consecutive administration in either order, wherein preferably there is a time period while both (or all) active agents simultaneously exert their biological activities.

In one embodiment, treatment with an anti-VEGF antibody (e.g., bevacizumab) involves the combined administration of an anti-cancer agent identified herein, and one or more chemotherapeutic agents (e.g., TMZ) or growth inhibitory agents, including co-administration of cocktails of different chemotherapeutic agents. Chemotherapeutic agents include taxanes (such as paclitaxel and docetaxel) and/or anthracycline antibiotics. Preparation and dosing schedules for such chemotherapeutic agents may be used according to manufacturer's instructions or as determined empirically by the skilled practitioner. Preparation and dosing schedules for such chemotherapy are also described in "Chemotherapy Service," (1992) Ed., M. C. Perry, Williams & Wilkins, Baltimore, Md.

Suitable dosages for any of the above co-administered agents are those presently used and may be lowered due to the combined action (synergy) of the anti-VEGF antibody (e.g., bevacizumab) and other chemotherapeutic agents or treatments.

The combination therapy may provide "synergy" and prove "synergistic," i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In general, for the prevention or treatment of disease, the appropriate dosage of the additional therapeutic agent will depend on the type of disease to be treated, the type of antibody, the severity and course of the disease, whether the anti-VEGF antibody (e.g., bevacizumab) and additional agents and/or therapies (e.g., TMZ and/or radiotherapy) are administered for preventive or therapeutic purposes, previous therapy, the patient's clinical history and response to the anti-VEGF antibody and additional agents and/or therapies, and the discretion of the attending physician. The anti-VEGF antibody and additional agents and/or therapies are suitably administered to the patient at one time or over a series of treatments. The anti-VEGF antibody is typically administered as set forth below. Depending on the type and severity of the disease, about 20 mg/m$^2$ to 600 mg/m$^2$ of the additional agent is an initial candidate dosage for administration to the patient, whether, for example, by one or more separate administrations, or by continuous infusion. One typical daily dosage might range from about or about 20 mg/m$^2$, 85 mg/m$^2$, 90 mg/m$^2$, 125 mg/m$^2$, 200 mg/m$^2$, 400 mg/m$^2$, 500 mg/m$^2$ or more, depending on the factors mentioned above. For repeated administrations over several days or longer, depending on the condition, the treatment is sustained until a desired suppression of disease symptoms occurs. Thus, one or more doses of about 20 mg/m$^2$, 85 mg/m$^2$, 90 mg/m$^2$, 125 mg/m$^2$, 200 mg/m$^2$, 400 mg/m$^2$, 500 mg/m$^2$, 600 mg/m$^2$ (or any combination thereof) may be administered to the patient. Such doses may be administered intermittently, e.g., every week or every two, three weeks, four, five, or six (e.g., such that the patient receives from about two to about twenty, e.g. about six doses of the additional agent). An initial higher loading dose, followed by one or more lower doses may be administered. However, other dosage regimens may be useful. The progress of this therapy is easily monitored by conventional techniques and assays.

In one embodiment, the subject has never been previously administered any drug(s) to treat glioblastoma. In another embodiment, the subject or patient has been previously administered one or more medicaments(s) to treat glioblastoma. In a further embodiment, the subject or patient was not responsive to one or more of the medicaments that had been previously administered. Such drugs to which the subject may be non-responsive include, for example, anti-neoplastic agents, chemotherapeutic agents, cytotoxic agents, and/or growth inhibitory agents, alone or in combination with one another, but in the absence of combined treatment with an anti-VEGF antibody, such as bevacizumab. Other therapies to which the subject may be non-responsive include, for example, VEGF antagonist montherapy, such as anti-VEGF antibody monotherapy.

The invention further provides a promotional method, comprising promoting the administration of an anti-VEGF antibody (e.g., bevacizumab) and one or more other therapeutic agents for treatment of glioblastoma (e.g., newly diagnosed glioblastoma and/or glioblastoma of the proneural type) in a human patient/subject. In some embodiments the method further comprises promoting the administration of at least one chemotherapeutic agent. Administration of the anti-VEGF antibody (e.g., bevacizumab) may be concurrent with or sequential to administration of a chemotherapeutic agent (e.g., TMZ). Promotion may be conducted by any means available. In some embodiments the promotion is by a package insert accompanying a commercial formulation of the anti-VEGF antibody. The promotion may also be by a package insert accompanying a commercial formulation of the chemotherapeutic agent. Promotion may be by written or oral communication to a physician or health care provider. In some embodiments the promotion is by a package insert where the package inset provides instructions to receive glioblastoma therapy with anti-VEGF antibody in combination with one or more other chemotherapeutics agents and/or therapies. In a further embodiment, the package insert include some or all of the results under Example 4. In some embodiments, the promotion is followed by the treatment of the subject with the anti-VEGF antibody (e.g., bevacizumab) with the chemotherapeutic agent (e.g., TMZ) and, optionally, another therapy (e.g., radiotherapy).

The invention provides a business method, comprising marketing an anti-VEGF antibody (e.g., bevacizumab) in combination with one or more other therapeutic agents, such as chemotherapeutics (e.g., TMZ), and/or therapies (e.g., radiotherapy), for treatment of glioblastoma in a human patient/subject so as to increase the subject's time for OS and/or PFS, to decrease the subject's likelihood of glioblastoma recurrence and/or increase the subject's likelihood of survival. In some embodiments the method further comprises marketing a chemotherapeutic agent for use in combination with the anti-VEGF antibody (e.g., bevacizumab). In some embodiments, the marketing is followed by treatment of the subject with the anti-VEGF antibody (e.g., bevacizumab) with the chemotherapeutic agent.

1. Dosage and Administration

The methods of treatment of the invention may result in, for example, a reduction in tumor size (e.g., glioblastoma tumor size), prolonged median overall survival (OS) time, and/or progression-free survival (PFS) time of the treated patient as compared to that of a patient who received the chemotherapeutic (e.g., TMZ) without an anti-VEGF antibody (e.g., bevacizumab). As described above, treatment with the combination of an anti-VEGF antibody (e.g., bevacizumab) and at least one additional medicament/therapy (e.g., chemotherapeutic, such as TMZ, and/or radiotherapy) may result in an additive or synergistic (greater than additive) therapeutic benefit to the patient.

The timing between at least one administration of the additional medicament/therapy (e.g., chemotherapeutic, such as TMZ, and/or, e.g., radiotherapy) and at least one administration of the anti-VEGF antibody (e.g., bevacizumab) herein is about one month or less, about two weeks or less, about one week or less, within the same day, within the same hour, or approximately the same (concurrent administration). In some instances, the at least one anti-VEGF antibody can be administered prior to the at least one additional medicament/therapy. In some instances, the at least one anti-VEGF antibody can be administered after the at least one additional medicament/therapy. In some instances the at least one anti-VEGF antibody and/or the at least one medicament/therapy are administered to the patient in one or more cycles (e.g., 1, 2, 3, 4, 5, 6, 7, 8, 9, 10, 11, 12, 13, 14, 15, 16, 17, 18, 19, 20, 25, 30, 35, 40, 45, 50, or more cycles).

It will be appreciated by those of skill in the medical arts that the exact manner of administering a therapeutically effective amount of an anti-VEGF antibody (e.g., bevacizumab) to a patient following diagnosis of glioblastoma will be at the discretion of the attending physician. For example, the glioblastoma may be newly diagnosed or not newly diagnosed, and the glioblastoma may be a recurrent glioblastoma.

The mode of administration, including dosage, combination with other agents, timing and frequency of administration, and the like, may be affected by the diagnosis of a patient's likely responsiveness to such anti-VEGF antibody (e.g., bevacizumab), as well as the patient's condition and history. Thus, even patients having glioblastomas who are predicted to be relatively insensitive to an anti-VEGF antibody alone may still benefit from treatment therewith, particularly in combination with other agents and/or therapies (e.g., chemotherapeutic, such as TMZ, and/or, e.g., radiotherapy) that may alter a patient's responsiveness to the anti-VEGF antibody.

A composition comprising an anti-VEGF antibody (e.g., bevacizumab) will be formulated, dosed, and administered in a fashion consistent with good medical practice. Factors for consideration in this context include the particular type of glioblastoma being treated (e.g., a newly diagnosed glioblastoma or a recurrent glioblastoma, a glioblastoma of the proneural type, a glioblastoma of the mesenchymal type, or a glioblastoma of the proliferative type), the particular mammal being treated (e.g., human), the clinical condition of the individual patient, the cause of the glioblastoma, the site of delivery of the agent, possible side-effects, the particular anti-VEGF antibody, the method of administration, the scheduling of administration, and other factors known to medical practitioners. The effective amount of the anti-VEGF antibody (e.g., bevacizumab) to be administered will be governed by such considerations.

A physician having ordinary skill in the art can readily determine and prescribe the effective amount of the pharmaceutical composition required, depending on such factors as the particular anti-VEGF antibody (e.g., bevacizumab). For example, the physician could start with doses of such an anti-VEGF antibody, employed in the pharmaceutical composition at levels lower than that required in order to achieve the desired therapeutic effect and gradually increase the dosage until the desired effect is achieved. The effectiveness of a given dose or treatment regimen of the antagonist can be determined, for example, by assessing signs and symptoms in the patient using standard measures of efficacy.

In certain examples, the patient is treated with the same anti-VEGF antibody (e.g., bevacizumab) at least twice. Thus, the initial and second anti-VEGF antibody exposures are with the same anti-VEGF antibody (e.g., bevacizumab), and, in some instances, all anti-VEGF antibody exposures are with the same anti-VEGF antibody, i.e., treatment for the first two exposures, and preferably all exposures, is with one type of anti-VEGF antibody, e.g., all with bevacizumab.

As a general proposition, the effective amount of the anti-VEGF antibody administered parenterally per dose will be in the range of about 20 mg to about 5000 mg, by one or more dosages. Exemplary dosage regimens for antibodies, such as anti-VEGF antibodies (e.g., bevacizumab), include 100 or 400 mg every 1, 2, 3, or 4 weeks or is administered a dose of about 1, 3, 5, 10, 15, or 20 mg/kg every 1, 2, 3, or 4 weeks. For example, an effective amount of an anti-VEGF antibody (e.g., bevacizumab) can be administered at 10 mg/kg every two weeks, optionally, by intravenous (i.v.) administration. In another example, an effective amount of an anti-VEGF antibody can be administered at 15 mg/kg every three weeks, optionally, by i.v. administration. The dose may be administered as a single dose or as multiple doses (e.g., 2 or 3 doses), such as infusions.

In some instances, depending on the type and severity of the disease, about 1 ug/kg to 100 mg/kg (e.g., 0.1-20 mg/kg) of the anti-VEGF antibody (e.g., bevacizumab) as an initial candidate dosage for administration to the subject, whether, for example, by one or more separate administrations, or by continuous infusion. In one embodiment, desirable dosages include, for example, 6 mg/kg, 8 mg/kg, 10 mg/kg, and 15 mg/kg. For repeated administrations or cycles over several days or longer, depending on the condition, the treatment is sustained until the cancer is treated, as measured by the methods described above or known in the art. However, other dosage regimens may be useful. In one example, the anti-VEGF antibody is administered once every week, every two weeks, or every three weeks, at a dose range from about 6 mg/kg to about 15 mg/kg, including but not limited to 6 mg/kg, 8 mg/kg, 10 mg/kg or 15 mg/kg. The progress of the therapy of the invention is easily monitored by conventional techniques and assays. In other embodiments, such dosing regimen is used in combination with a chemotherapy regimen in glioblastoma. Further information about suitable dosages is provided in the Example below.

The duration of therapy can be continued for as long as medically indicated or until a desired therapeutic effect (e.g., those described herein) is achieved. In certain embodiments, the therapy is continued for 1 month, 2 months, 4 months, 6 months, 8 months, 10 months, 1 year, 2 years, 3 years, 4 years, 5 years, or for a period of years up to the lifetime of the subject.

If multiple exposures of anti-VEGF antibody are provided, each exposure may be provided using the same or a different administration means. In one embodiment, each exposure is by intravenous (i.v.) administration. In another embodiment, each exposure is given by subcutaneous (s.c.) administration. In yet another embodiment, the exposures are given by both i.v. and s.c. administration.

In one embodiment, the anti-VEGF antibody (e.g., bevacizumab) is administered as a slow intravenous infusion rather than an intravenous push or bolus. For example, a steroid such as prednisolone or methylprednisolone (e.g., about 80-120 mg i.v., more specifically about 100 mg i.v.) is administered about 30 minutes prior to any infusion of the anti-VEGF antibody. For example, an anti-VEGF antibody, such as bevacizumab, can be infused through a dedicated line. For example, an anti-VEGF antibody, such as bevacizumab, can be administered initially intravenously over about 90 minutes, with subsequent infusions over about 60 minutes and then about 30 minutes.

For the initial dose of a multi-dose exposure to an anti-VEGF antibody (e.g., bevacizumab), or for the single dose if the exposure involves only one dose, such infusion is preferably commenced at a rate of about 50 mg/hour. This may be escalated, e.g., at a rate of about 50 mg/hour increments every about 30 minutes to a maximum of about 400 mg/hour. However, if the subject is experiencing an infusion-related reaction, the infusion rate is preferably reduced, e.g., to half the current rate, e.g., from 100 mg/hour to 50 mg/hour. For example, the infusion of such dose of anti-VEGF antibody (e.g., an about 1000-mg total dose) is completed at about 255 minutes (4 hours 15 min.). Optionally, the subjects receive a prophylactic treatment of acet-aminophen/paracetamol (e.g., about 1 g) and diphenhydramine HCl (e.g., about 50 mg or equivalent dose of similar agent) by mouth about 30 to 60 minutes prior to the start of an infusion.

If more than one infusion (dose) of an anti-VEGF antibody (e.g., bevacizumab) is given to achieve the total exposure, the second or subsequent anti-VEGF antibody infusions in this embodiment are commenced at a higher rate than the initial infusion, e.g., at about 100 mg/hour. This rate may be escalated, e.g., at a rate of about 100 mg/hour increments every about 30 minutes to a maximum of about 400 mg/hour. Subjects who experience an infusion-related reaction preferably have the infusion rate reduced to half that rate, e.g., from 100 mg/hour to 50 mg/hour. Preferably, the infusion of such second or subsequent dose of anti-VEGF antibody (e.g., an about 1000-mg total dose) is completed by about 195 minutes (3 hours 15 minutes).

In one embodiment, the anti-VEGF antibody (e.g., bevacizumab) and is administered in a dose of about 0.4 to 4 grams, and more preferably the antibody is administered in a dose of about 0.4 to 1.3 grams at a frequency of one to four doses within a period of about one month. Still more preferably, the dose is about 500 mg to 1.2 grams, and in other embodiments is about 750 mg to 1.1 grams. In such aspects, the anti-VEGF antibody is preferably administered in two to three doses, and/or is administered within a period of about 2 to 3 weeks.

As noted above, however, these suggested amounts of anti-VEGF antibody are subject to a great deal of therapeutic discretion. The key factor in selecting an appropriate dose and scheduling is the result obtained, as indicated above. In some embodiments, the anti-VEGF antibody is administered as close to the first sign, diagnosis, appearance, or occurrence of the glioblastoma as possible.

2. Routes of Administration

The anti-VEGF antibody (e.g., bevacizumab) can be administered by any suitable means, including parenteral, topical, subcutaneous, intraperitoneal, intrapulmonary, intranasal, and/or intralesional administration. Parenteral infusions include intramuscular, intravenous, intraarterial, intraperitoneal, or subcutaneous administration. Intrathecal administration is also contemplated. In addition, the anti-VEGF antibody may suitably be administered by pulse infusion, e.g., with declining doses of the anti-VEGF antibody. Most preferably, the dosing is given by intravenous (i.v.) injections/infusions.

Aside from administration of anti-VEGF antibodies to the patient by traditional routes as noted above, the present invention includes administration by gene therapy. See, for example, WO 1996/07321, concerning the use of gene therapy to generate intracellular antibodies, such as anti-VEGF antibodies.

There are two major approaches to getting the nucleic acid (optionally contained in a vector) into the patient's cells: in vivo and ex vivo. For in vivo delivery the nucleic acid is injected directly into the patient, usually at the site where the antagonist is required. For ex vivo treatment, the patient's cells are removed, the nucleic acid is introduced into these isolated cells and the modified cells are administered to the patient either directly, or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent specific for the target cells, such as an antibody specific for a cell-surface membrane protein on the target cell, a ligand for a receptor on the target cell, etc. Where liposomes are employed, proteins that bind to a cell-surface membrane protein associated with endocytosis may be used for targeting and/or to facilitate uptake, e.g., capsid proteins or fragments thereof tropic for a particular cell type, antibodies for proteins that undergo internalization in cycling, and proteins that target intracellular localization and enhance intracellular half-life. The technique of receptor-mediated endocytosis is described, for example, by Wu et al., *J. Biol. Chem.* 262: 4429-4432 (1987); and Wagner et al., *PNAS USA* 87:3410-3414 (1990). Gene-marking and gene-therapy protocols are described, for example, in Anderson et al., *Science* 256:808-813 (1992) and WO 1993/25673.

B. Anti-VEGF Antibodies

In all the methods of treatment set forth herein, the anti-VEGF antibody binds to VEGF with sufficient specificity and affinity and may be a chimeric, humanized, human, or library-derived antibody, or antibody fragment thereof.

1. Chimeric and Humanized Antibodies

In certain embodiments, the anti-VEGF antibody may be a chimeric antibody. Certain chimeric antibodies are described, e.g., in U.S. Pat. No. 4,816,567 and Morrison et al. *PNAS USA,* 81:6851-6855, 1984). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, the anti-VEGF antibody may be a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity. Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

2. Human Antibodies

In certain embodiments, the anti-VEGF antibody may be a human antibody. Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. PNAS USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008). Human antibodies may be prepared, for example, by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., PNAS USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

In some instances, human antibodies may also be generated by isolating Fv clone variable domain sequences selected from human-derived phage display libraries. Such variable domain sequences may then be combined with a desired human constant domain.

3. Library-Derived Antibodies

In certain embodiments, the anti-VEGF antibody may be, or have been, isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178:1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, PNAS USA 101(34): 12467-12472 (2004); and Lee et al., J. Immunol. Methods 284(1-2): 119-132(2004).

In some phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

4. Antibody Production and Properties

The anti-VEGF antibodies that are useful in the methods of the invention can include any antibody, or antigen binding fragment thereof, that binds with sufficient affinity and specificity to VEGF and/or that can reduce or inhibit the biological activity of VEGF. An anti-VEGF antibody will usually not bind to other VEGF homologues such as VEGF-B or VEGF-C, nor other growth factors such as PIGF, PDGF, or bFGF.

In some instances, the VEGF antigen to be used for production of VEGF antibodies may be, e.g., the $VEGF_{165}$ molecule as well as other isoforms of VEGF or a fragment thereof containing the desired epitope. In one embodiment, the desired epitope is the one recognized by bevacizumab, which binds to the same epitope as the monoclonal anti-VEGF antibody A4.6.1 produced by hybridoma ATCC HB 10709 (known as "epitope A.4.6.1" defined herein). Other forms of VEGF useful for generating anti-VEGF antibodies of the invention will be apparent to those skilled in the art.

Human VEGF was obtained by first screening a cDNA library prepared from human cells, using bovine VEGF cDNA as a hybridization probe. Leung et al. (1989) Science, 246:1306. One cDNA identified thereby encodes a 165-amino acid protein having greater than 95% homology to bovine VEGF; this 165-amino acid protein is typically referred to as human VEGF (hVEGF) or $VEGF_{165}$ The mitogenic activity of human VEGF was confirmed by expressing the human VEGF cDNA in mammalian host cells. Media conditioned by cells transfected with the human VEGF cDNA promoted the proliferation of capillary endothelial cells, whereas control cells did not. Leung et al. (1989) Science, supra. Further efforts were undertaken to clone and express VEGF via recombinant DNA techniques. (See, e.g., Ferrara, Laboratory Investigation 72:615-618 (1995), and the references cited therein).

VEGF is expressed in a variety of tissues as multiple homodimeric forms (121, 145, 165, 189, and 206 amino acids per monomer) resulting from alternative RNA splicing. $VEGF_{121}$ is a soluble mitogen that does not bind heparin; the longer forms of VEGF bind heparin with progressively higher affinity. The heparin-binding forms of VEGF can be cleaved in the carboxy terminus by plasm in to release a diffusible form(s) of VEGF. Amino acid sequencing of the carboxy terminal peptide identified after plasmin cleavage is $Arg_{110}$-$Ala_{111}$. Amino terminal "core" protein, VEGF (1-110) isolated as a homodimer, binds neutralizing monoclonal antibodies (such as the antibodies referred to as 4.6.1 and 3.2E3.1.1) and soluble forms of VEGF receptors with similar affinity compared to the intact VEGF$_{165}$ homodimer.

Several molecules structurally related to VEGF have also been identified recently, including placenta growth factor (PlGF), VEGF-B, VEGF-C, VEGF-D and VEGF-E. Ferrara and Davis-Smyth (1987) Endocr. Rev., supra; Ogawa et al. J. Biological Chem. 273:31273-31281 (1998); Meyer et al. EMBO J., 18:363-374 (1999). A receptor tyrosine kinase, Flt-4 (VEGFR-3), has been identified as the receptor for VEGF-C and VEGF-D. Joukov et al. EMBO. J. 15:1751 (1996); Lee et al. PNAS USA 93:1988-1992 (1996); Achen et al. (1998) PNAS USA 95:548-553. VEGF-C has been shown to be involved in the regulation of lymphatic angiogenesis. Jeltsch et al. Science 276:1423-1425 (1997).

Two VEGF receptors have been identified, Flt-1 (also called VEGFR-1) and KDR (also called VEGFR-2). Shibuya et al. (1990) Oncogene 8:519-527; de Vries et al. (1992) Science 255:989-991; Terman et al. (1992) Biochem. Biophys. Res. Commun. 187:1579-1586. Neuropilin-1 has been shown to be a selective VEGF receptor, able to bind the heparin-binding VEGF isoforms (Soker et al. (1998) Cell 92:735-45).

In certain embodiments of the invention, the anti-VEGF antibodies include, but are not limited to, a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al. (1997) Cancer Res. 57:4593-4599. In one embodiment, the anti-VEGF antibody is bevacizumab (BV or Bev), also known as "rhuMAb VEGF" or "AVASTIN®." It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of bevacizumab, including most of the framework regions, is derived from human IgG1, and about 7% of the sequence is derived from the murine antibody A4.6.1.

Bevacizumab (AVASTIN®) was the first anti-angiogenesis therapy approved by the FDA and is approved for the treatment metastatic colorectal cancer (first- and second-line treatment in combination with intravenous 5-FU-based chemotherapy), advanced non-squamous, non-small cell lung cancer (NSCLC) (first-line treatment of unresectable, locally advanced, recurrent or metastatic NSCLC in combination with carboplatin and paclitaxel) and metastatic HER2-negative breast cancer (previously untreated, metastatic HER2-negative breast cancer in combination with paclitaxel).

Bevacizumab and other humanized anti-VEGF antibodies are described in U.S. Pat. No. 6,884,879 issued Feb. 26, 2005. Additional antibodies include the G6 or B20 series antibodies (e.g., G6-31, B20-4.1), as described in PCT Publication No. WO2005/012359, PCT Publication No. WO2005/044853, and U.S. Patent Application 60/991,302, the content of these patent applications are expressly incorporated herein by reference.

A G6 series antibody according to this invention, is an anti-VEGF antibody that is derived from a sequence of a G6 antibody or G6-derived antibody according to any one of FIGS. 7, 24-26, and 34-35 of PCT Publication No. WO2005/012359, the entire disclosure of which is expressly incorporated herein by reference. See also PCT Publication No. WO2005/044853, the entire disclosure of which is expressly incorporated herein by reference. In one embodiment, the G6 series antibody binds to a functional epitope on human VEGF comprising residues F17, Y21, Q22, Y25, D63, I83 and Q89.

A B20 series antibody according to this invention is an anti-VEGF antibody that is derived from a sequence of the B20 antibody or a B20-derived antibody according to any one of FIGS. 27-29 of PCT Publication No. WO2005/012359, the entire disclosure of which is expressly incorporated herein by reference. See also PCT Publication No. WO2005/044853, and U.S. Patent Application 60/991,302, the content of these patent applications are expressly incorporated herein by reference. In one embodiment, the B20 series antibody binds to a functional epitope, as defined above, on human VEGF comprising residues F17, M18, D19, Y21, Y25, Q89, I91, K101, E103, and C104.

In other embodiments, other anti-VEGF antibodies are used in the combination therapy described above, either as the sole anti-VEGF antibody or in addition to use of an anti-VEGF antibody described above. Such antibodies are described, for example, in U.S. Pat. Nos. 7,060,269, 6,582,959, 6,703,020; 6,054,297; WO98/45332; WO 96/30046; WO94/10202; EP 0666868B1; U.S. Patent Application Publication Nos. 2006009360, 20050186208, 20030206899, 20030190317, 20030203409, and 20050112126; and Popkov et al., Journal of Immunological Methods 288:149-164 (2004). These other antibodies may include those that bind to a functional epitope, as defined above, on human VEGF comprising of residues F17, M18, D19, Y21, Y25, Q89, I191, K101, E103, and C104, or, alternatively, comprising residues F17, Y21, Q22, Y25, D63, I83 and Q89.

In some embodiments, an anti-VEGF antibody useful in any one of the methods described herein may have a light chain variable region comprising the following amino acid sequence:

```
                                             (SEQ ID NO: 1)
DIQMTQSPSS LSASVGDRVT ITCSASQDIS NYLNWYQQKP

GKAPKVLIYF TSSLHSGVPS RFSGSGSGTD FTLTISSLQP

EDFATYYCQQ YSTVPWTFGQ GTKVEIKR,
``` and a heavy chain variable region comprising the following amino acid sequence:

```
                                             (SEQ ID NO: 2)
EVQLVESGGG LVQPGGSLRL SCAASGYTFT NYGMNWVRQA

PGKGLEWVGW INTYTGEPTY AADFKRRFTF SLDTSKSTAY

LQMNSLRAED TAVYYCAKYP HYYGSSHWYF DVWGQGTLVT VSS.
```

In yet other embodiments, the anti-VEGF antibody may be unconjugated, such as a naked anti-VEGF antibody, or may be conjugated with another molecule for further effectiveness, such as, for example, to improve half-life. In any of the methods and uses, the conjugated antibody and/or antigen to which it is bound is/are internalized by the cell, resulting in increased therapeutic efficacy of the conjugate in killing the cancer cell (e.g., glioblastoma cancer cell) to which it binds. For example, the cytotoxic agent may target or interfere with nucleic acid in the cancer cell. Examples of such cytotoxic agents include maytansinoids, calicheamicins, ribonucleases and DNA endonucleases.

IV. Pharmaceutical Formulations

Therapeutic formulations of the antibodies used described herein, used in accordance with the present invention, are prepared for storage by mixing an antibody having the desired degree of purity with optional pharmaceutically acceptable carriers, excipients, or stabilizers in the form of lyophilized formulations or aqueous solutions. For general information concerning formulations, see, e.g., Gilman et al., (eds.) (1990), *The Pharmacological Bases of Therapeutics*, 8th Ed., Pergamon Press; A. Gennaro (ed.), Remington's Pharmaceutical Sciences, 18th Edition, (1990), Mack Publishing Co., Eastori, Pa.; Avis et al., (eds.) (1993) *Pharmaceutical Dosage Forms: Parenteral Medications* Dekker, N.Y.; Lieberman et al., (eds.) (1990) *Pharmaceutical Dosage Forms: Tablets* Dekker, New York; and Lieberman et al., (eds.) (1990), *Pharmaceutical Dosage Forms: Disperse Systems* Dekker, New York, Kenneth A. Walters (ed.) (2002) *Dermatological and Transdermal Formulations* (Drugs and the Pharmaceutical Sciences), Vol 119, Marcel Dekker.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG).

Exemplary anti-VEGF antibody formulations are described in U.S. Pat. No. 6,884,879. In certain embodiments anti-VEGF antibodies are formulated at 25 mg/mL in single use vials. In certain embodiments, 100 mg of the anti-VEGF antibodies are formulated in 240 mg α,α-trehalose dihydrate, 23.2 mg sodium phosphate (monobasic, monohydrate), 4.8 mg sodium phosphate (dibasic anhydrous), 1.6 mg polysorbate 20, and water for injection, USP. In certain embodiments, 400 mg of the anti-VEGF antibodies are formulated in 960 mg α,α-trehalose dihydrate, 92.8 mg sodium phosphate (monobasic, monohydrate), 19.2 mg sodium phosphate (dibasic anhydrous), 6.4 mg polysorbate 20, and water for injection, USP. Lyophilized formulations adapted for subcutaneous administration are described, for example, in U.S. Pat. No. 6,267,958 (Andya et al.). Such lyophilized formulations may be reconstituted with a suitable diluent to a high protein concentration and the reconstituted formulation may be administered subcutaneously to the mammal to be treated herein.

Crystallized forms of the antagonist are also contemplated. See, for example, US 2002/0136719A1.

The formulation herein may also contain more than one active compound (a second medicament as noted above), preferably those with complementary activities that do not adversely affect each other. The type and effective amounts of such medicaments depend, for example, on the amount and type of VEGF antagonist (e.g., an anti-VEGF antibody, e.g., bevacizumab) present in the formulation, and clinical parameters of the subjects. The preferred such second medicaments are noted above.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antagonist, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

V. Kits

In another aspect of the invention, an article of manufacture containing materials useful for the treatment of a patient diagnosed with a glioblastoma (e.g., a newly diagnosed glioblastoma and/or a glioblastoma of the proneural type) is provided. The article of manufacture comprises a container, a label and a package insert. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is an anti-VEGF antibody (e.g., bevacizumab). The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, and syringes. In addition, the article of manufacture comprises a package inserts with instructions for use, including for example instructing the user of the composition to administer the anti-VEGF antibody (e.g., bevacizumab) composition and a chemotherapeutic agent (e.g., TMZ) to the patient/subject. The package insert may optionally contain some or all of the results found in Example 4.

The anti-VEGF antibody can be packaged alone or in combination with other anti-cancer therapeutic compounds as a kit. The kit can include optional components that aid in the administration of the unit dose to subjects, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one subject or multiple uses for a particular subject (at a constant dose or in which the individual compounds may vary in potency as therapy progresses). The kit may contain multiple doses suitable for administration to multiple subjects ("bulk packaging"). The kit components may be assembled in cartons, blister packs, bottles, tubes, and the like.

In some embodiments, the kit is for intended use on a patient who has received two or fewer (e.g., two, one, or zero) prior anti-cancer regimens.

EXAMPLES

The following examples are provided to illustrate, but not to limit the presently claimed invention.

Example 1. AvaGlio Study

The AvaGlio trial evaluated the efficacy and safety of bevacizumab in combination temozolomide and radiotherapy for newly diagnosed glioblastoma. This study was designed as a prospective, randomized, double blind, placebo controlled Phase III evaluation of bevacizumab plus chemotherapy versus chemotherapy alone. To be eligible, patients must have had newly diagnosed glioblastoma with a tissue diagnosis that has been established following either a surgical resection or biopsy. By adding bevacizumab to chemotherapy and radiotherapy, the AvaGlio trial aimed to improve overall survival (OS) and progression-free survival (PFS) for this group of patients who had limited therapeutic options and faced a particularly poor prognosis. The primary objective was to compare OS and PFS of patients randomized to temozolomide (TMZ) and radiotherapy only or to temozolomide and radiotherapy plus bevacizumab.

Overview of AvaGlio Study

This trial consisted of three phases (Concurrent, Maintenance, and Monotherapy) and two (2) treatment arms: TMZ and radiotherapy (RT) (Arm 1), and TMZ and RT plus bevacizumab (Arm 2). Patients were randomly assigned (1:1) to either arm. See FIG. 1.

Arm 1 (chemotherapy and radiotherapy alone): Eligible patients received 2 Gy RT 5 days a week for 6 weeks and 75 mg/m$^2$ TMZ orally daily for 6 weeks from the first day to the last day of RT in combination with 10 mg/kg placebo i.v. every 2 weeks. After a 4-week treatment break, eligible patients received 6 cycles of 150-200 mg/m$^2$ TMZ on days 1-5 of an every-4-week schedule in combination with 10 mg/kg placebo i.v. every 2 weeks. TMZ was administered orally starting with a 150 mg/m$^2$ dose that could be escalated. Placebo monotherapy (15 mg/kg every 3 weeks) was then continued until disease progression. Upon disease progression, patients were treated at the investigator's discretion.

Arm 2 (chemotherapy and radiotherapy plus bevacizumab): Eligible patients received 2 Gy RT 5 days a week for 6 weeks and 75 mg/m$^2$ TMZ orally daily for 6 weeks from the first day to the last day of RT in combination with 10 mg/kg bevacizumab i.v. every 2 weeks. After a 4-week treatment break, eligible patients received 6 cycles of 150-200 mg/m$^2$ TMZ on days 1-5 of an every-4-week schedule in combination with 10 mg/kg bevaciumab i.v. every 2 weeks. TMZ was administered orally starting with a 150 mg/m$^2$ dose that could be escalated. Bevaciazumab monotherapy (15 mg/kg every 3 weeks) was then continued until disease progression. Upon disease progression, patients were treated at the investigator's discretion.

The initial bevacizumab infusion was over 90 minutes, with subsequent infusions over 60 minutes and then 30 minutes, as tolerated. Bevacizumab was administered on the last day of RT and TMZ treatment, i.e., the day before the start of the TMZ treatment break.

Analyses of PFS were based on tumor assessments MacDonald Response Criteria (modified WHO criteria) using MRI of the brain and a neurological evalution as described in Macdonald et al. (*J. Clin. Oncol.* 8: 1277-80, 1990). Tumor assessments were performed at baseline, at the end of the 4-week treatment break, then every 8 weeks.

Study Population—Inclusion Criteria

Patients ≥8 years of age and with newly diagnosed supratentorial Glioblastoma (GBM) with a tissue diagnosis that had been established following either a surgical resection or biopsy were included. This includes treatment-naïve chemotherapy and radiotherapy patients with prior diagnosis of a lower grade astrocytoma that had been upgraded to a histologically verified GBM. Patients must have had WHO performance status 2.

Study Population—Exclusion Criteria

Evidence of recent hemorrhage on post-operative MRI of the brain excluded candidate patients. However, patients with clinically asymptomatic presence of hemosiderin, resolving hemorrhagic changes related to surgery, and presence of punctate hemorrhage in the tumor were permitted entry into the study. Previous centralized screening for MGMT status for enrollment into a clinical trial; any prior chemotherapy (including carmustine-containing wafers (Gliadel®) or immunotherapy (including vaccine therapy) for glioblastomas and low grade astrocytomas; any prior radiotherapy to the brain or prior radiotherapy resulting in a potential overlap in the radiation field; prior history of hypertensive crisis or hypertensive encephalopathy; history of ≥grade 2 haemoptysis according to the NCI-CTC criteria within 1 month prior to randomization; evidence of bleeding diathesis or coagulopathy (in the absence of therapeutic anticoagulation); major surgical procedure, open biopsy, intracranial biopsy, ventriculoperitoneal shunt or significant traumatic injury within 28 days prior to randomization; core biopsy (excluding intracranial biopsy) or other minor surgical procedure within 7 days prior to randomization also excluded patients. Placement of a central vascular access device (CVAD) if performed within 2 days prior to bevacizumab/placebo administration; history of abdominal fistula or gastrointestinal perforation within 6 months prior to randomization history of intracranial abscess within 6 months prior to randomization; serious non-healing wound, active ulcer, or untreated bone fracture also excluded patients. With respect to pregnant or lactating females, serum pregnancy tests were assessed within 7 days prior to study treatment start, or within 14 days (with a confirmatory urine pregnancy test within 7 days prior to study treatment start). Also excluded were fertile women (defined as <2 years after last menstruation and not surgically sterile) and men not using highly-effective, hormonal or non-hormonal means of contraception (i.e. intrauterine contraceptive device); patients with a history of stroke or transient ischemic attack (TIA) within months prior to randomization, inadequately controlled hypertension (sustained systolic >150 mmHg and/or diastolic >100 mmHg) or significant vascular disease, including aortic aneurysm requiring surgical repair or recent peripheral arterial thrombosis, within months prior to randomization. Also excluded were patients who had myocardial infarction or unstable angina within months prior to randomization, New York Heart Association (NYHA) grade II or greater congestive heart failure (CHF), or known hypersensitivity to any of the study drugs or excipients.

Example 2. Categorizing FFPE-Fixed Samples Using Nanostring Gene Expression Data Stratification of clinical samples into gene expression subtypes is complicated by the fact that standard sample preparation, e.g., fixation using formalin-fixed, paraffin-embedded (FFPE) techniques, reduces the quality and amount of RNA available for analysis using standard methods, e.g. microarrays. Recently, single-molecule analysis technologies, e.g. the Nanostring nCounter (Geiss et al. *Biotechnol.* 26(3): 317-325, 2008), have become available to assay gene expression in FFPE-fixed material.

To assign patient-derived samples into gene expression subtypes originally defined from fresh-frozen samples analyzed on microarrays, we applied a four-step approach. Specifically, we:
1. Re-normalized published microarray data for 98 samples classified by Lai et al and calculated the gene expression centroids for the 35 classifier genes (reference data).
2. Applied the centroids to classify a new set of 47 glioblastoma samples analyzed on the same Affymetrix microarray platform (normalized to the same reference distribution as the reference data) (training samples).
3. Profiled the expression of the classifier genes in the same 47 training samples on the Nanostring nCounter system.
4. Recalibrated the centroids for the Nanostring platform using the subtype labels assigned to the 47 training samples based on the Affymetrix microarray data.

We obtained three centroids for the Nanostring platform, one for each subtype, which could be applied to directly classify novel samples only assayed on this technology platform.

Obtaining Gene Expression Centroids for Affymetrix Microarray Data

We obtained the raw expression data for 98 samples analyzed and classified by Lai et al (*Clin. Oncol.* 29(34): 4482-4490, 2011) on hgu133plus2 Affymetrix microarrays from Genentech's research database, normalized the data (to make it comparable across arrays) and stored the reference distribution (Harbron et al. *Bioinformatics.* 23(18): 2493-2494, 2007).

As shown below in Table 1, we subset the data to the 35 microarray classifier probes (of which 30 are associated with annotated genes at the time of writing) and associated each sample with the subtype label assigned by Lai et al.

TABLE 1

Centroids for expression subtypes defined by Phillips et al. determined from normalized Affymetrix expression data published by Lai et al.

|  | Mes | PN | Prolif |
|---|---|---|---|
| 205266_at | 8.51 | 7.17 | 7.42 |
| 235417_at | 10.25 | 8.48 | 8.85 |
| 223333_s_at | 8.87 | 7.53 | 7.38 |
| 205547_s_at | 11.57 | 9.20 | 10.03 |
| 202628_s_at | 10.63 | 8.47 | 8.94 |
| 201058_s_at | 9.52 | 7.66 | 8.35 |
| 211966_at | 9.83 | 8.23 | 8.57 |
| 226658_at | 10.48 | 9.12 | 9.60 |
| 211981_at | 10.94 | 9.30 | 9.84 |
| 229438_at | 7.87 | 7.13 | 7.17 |
| 201666_at | 13.61 | 11.86 | 12.78 |

TABLE 1-continued

Centroids for expression subtypes defined by Phillips et al. determined from normalized Affymetrix expression data published by Lai et al.

|  | Mes | PN | Prolif |
|---|---|---|---|
| 209396_s_at | 13.51 | 11.18 | 12.49 |
| 215870_s_at | 9.82 | 8.02 | 9.85 |
| 211564_s_at | 9.32 | 7.09 | 9.06 |
| 218880_at | 8.69 | 7.29 | 7.27 |
| 228033_at | 7.12 | 6.78 | 8.13 |
| 222848_at | 8.10 | 8.32 | 9.37 |
| 207165_at | 8.43 | 8.46 | 9.20 |
| 229490_s_at | 7.43 | 7.32 | 7.40 |
| 218585_s_at | 8.25 | 8.73 | 9.25 |
| 209981_at | 7.66 | 8.21 | 7.55 |
| 207723_s_at | 6.04 | 8.35 | 6.40 |
| 227984_at | 8.50 | 10.26 | 8.87 |
| 219537_x_at | 8.23 | 9.95 | 8.36 |
| 218796_at | 7.76 | 8.67 | 7.34 |
| 243779_at | 5.69 | 6.98 | 5.34 |
| 214952_at | 6.96 | 7.61 | 6.50 |
| 206850_at | 7.71 | 8.42 | 7.67 |
| 204953_at | 7.10 | 8.48 | 6.50 |
| 214279_s_at | 9.28 | 10.60 | 9.86 |
| 226913_s_at | 9.63 | 11.50 | 10.51 |
| 232833_at | 5.74 | 7.14 | 6.33 |
| 214762_at | 8.63 | 9.51 | 8.70 |
| 203146_s_at | 8.90 | 9.99 | 9.10 |
| 219196_at | 7.94 | 9.31 | 9.40 |

To obtain the three subtype-specific centroids, we averaged the expression of each gene individually for all samples assigned to a given subtype by calculating the mean (Table 1). In addition, we also stored the mean and standard deviation for each classifier probe observed across the full dataset. This reference dataset contained 38 Mesenchymal (Mes), 30 Proneural (PN), and 30 Proliferative (Profit) samples, as classified by Lai et al. (Table 2).

TABLE 2

Number of samples per subtype available in the reference dataset

|  | Number of Samples |
|---|---|
| Mes | 38 |
| PN | 30 |
| Prolif | 30 |

Classification of Glioblastoma Samples Cross-Analyzed on Affymetrix Microarrays and the Nanostring nCounter Next, we obtained raw microarray data from Genentech's research database for 47 new glioblastoma samples (training samples), which had also been analyzed on the Nanostring nCounter system. Each microarray was normalized to the same reference distribution as those processed above to ensure comparability between studies.

To associate the training samples with the subtypes defined by Phillips et al. (*Cancer Cell.* 9(3): 157-173, 2006), we subset the expression data to the same 35 classifier probes (corresponding to 30 annotated protein-coding genes) and scaled each probe's expression to match the mean and standard deviation observed for the same probe in the reference dataset.

For each sample, we determined the Pearson correlation coefficient to each of the three expression centroids defined above and assigned it to the subtype with the highest non-negative correlation coefficient. Samples without positive correlation to any of the centroids were left unassigned.

Of the 47 samples, 26 were classified as Mea, 14 as PN, and 7 as Prolif (Table 3).

TABLE 3
Number of samples per subtype available in the training dataset

| | Number of Samples |
|---|---|
| Mes | 26 |
| PN | 14 |
| Prolif | 7 |

Obtaining Subtype-Specific Centroids for the Nanostring nCounter Platform

The same 47 training samples were also analyzed on the Nanostring nCounter, featuring probes targeting the following 30 classifier genes, representing all of the original 35 microarray probes currently matched to protein-coding loci: ANGPTL4, ATP6V1G2, CENPK, CHI3LI, COL4AI, COL4A2, CSDC2, DLL3, DTL, E2F7, FOSL2, GABBR1, GALNT13, HMMR, KLRC3, LIF, MYL9, NCAM1, NDRG2, PDLIM4, PDPN, PLA2G5, RASL10A, SCG3, SERPINE1, SNAP91, SOX8, SPOCDI, TAGLN and TIMP1.

The raw Nanostring counts obtained from the nCounter analyzed software was log 2 transformed and normalized across samples by adjusting the mean and the standard deviation of the expression across all assayed probes to the same reference values. To define Nanostring-specific centroids for the three subtypes, we again calculated the mean expression for each classifier gene for each of the three subtypes (Table 4).

TABLE 4
Nanostring-specific centroids for Phillips expression subtypes

| Gene name | Mes | PN | Prolif |
|---|---|---|---|
| ANGPTL4 | 0.13 | −0.66 | −0.82 |
| ATP6V1G2 | −0.20 | 1.41 | 0.35 |
| CENPK | −0.32 | 0.31 | 1.21 |
| CHI3LI | 0.30 | −1.08 | −0.16 |
| COL4AI | −0.87 | −1.77 | −0.91 |
| COL4A2 | −1.09 | −1.96 | −0.94 |
| CSDC2 | −0.48 | 0.34 | −0.60 |
| DLL3 | −0.30 | 0.56 | 0.37 |
| DTL | −0.39 | 0.51 | 0.99 |
| E2F7 | −0.48 | −0.18 | 0.04 |
| FOSL2 | −0.51 | −1.77 | −1.44 |
| GABBR1 | −0.67 | 0.62 | −0.58 |
| GALNT13 | 0.12 | 0.90 | −0.72 |
| HMMR | −0.11 | 0.10 | 0.27 |
| KLRC3 | −0.19 | 1.15 | 0.53 |
| LIF | 0.08 | −1.39 | −0.77 |
| MYL9 | −0.15 | −.148 | −1.41 |
| NCAM1 | −0.04 | 1.08 | 0.14 |
| NDRG2 | 0.21 | 0.87 | 0.20 |
| PDLIM4 | −0.27 | −0.58 | −0.48 |
| PDPN | 0.56 | −0.65 | 0.21 |
| PLA2G5 | 0.24 | −0.33 | 0.32 |
| RASL10A | −0.28 | 0.98 | 0.01 |
| SCG3 | −0.61 | .065 | −0.31 |
| SERPINE1 | 0.24 | −0.91 | −0.28 |
| SNAP91 | −0.11 | 1.26 | −0.04 |
| SOX8 | −0.44 | 0.78 | 0.33 |
| SPOCDI | 0.16 | −1.17 | −0.25 |
| TAGLN | 0.11 | −1.29 | −0.59 |
| TIMP1 | 0.49 | −0.96 | −0.20 |

As above, samples were assigned to the subtype showing the highest Pearson correlation. To benchmark the accuracy of the Nanostring-based subtype assignments, we compared the recall of the original, microarray-based class labels. We observed concordant assignments for 38/47(80.1%) of the samples (Table 5).

TABLE 5
Recall of Nanostring-based subtype assignments for the training dataset

| | Mes | PN | Prolif |
|---|---|---|---|
| Mes | 20 | 1 | 0 |
| PN | 4 | 12 | 1 |
| Prolif | 2 | 1 | 6 |

To reduce the number of false assignments, more stringent filters for subtype assignments could be put into place, e.g., requiring a minimum positive Pearson correlation to classify a sample.

Example 3. Nanostring-Based Classification of Samples from the AvaGlio Trial

Next, we classified the 349 samples from the AvaGlio trial for which biomarkers could be evaluated into the gene expression subtypes defined by Phillips (Cancer Cell. 9(3): 157-173, 2006). Selected baseline characteristics of the 349 biomarker evaluable patients within each treatment arm are shown in Table 6.

TABLE 6
Selected baseline characteristics of biomarker evaluable patients

| | | Biomarker Evaluable Patients | |
|---|---|---|---|
| Patients, % | | RT/TMZ/PLB (n = 178) | RT/TMZ/BEV (n = 171) |
| Median age, years (range) | | 58 (21-79) | 59 (28-84) |
| Gender | Male | 64 | 60 |
| | Female | 36 | 40 |
| WHO PS | 0 | 50 | 47 |
| | 1-2 | 47 | 49 |
| RPA class - CRF | III | 12 | 14 |
| | IV | 63 | 59 |
| | V | 22 | 24 |
| MGMT status | Methylated | 26 | 23 |
| | Non-methylated | 49 | 56 |
| Surgical status | Biopsy | 6 | 6 |
| | Partial resection | 52 | 44 |
| | Complete resection | 39 | 46 |
| KPS | 50-80 | 32 | 32 |
| | 90-100 | 65 | 64 |
| MMSE score | <27 | 22 | 22 |
| | ≥27 | 75 | 73 |
| Corticosteroids | On | 47 | 40 |
| | Off | 49 | 54 |

Samples were analyzed with the same Nanostring probe set used to derive the subtype-specific centroids and expression scores for the same genes were obtained using the same technology and probe sequences. Of the 349 samples, 10 samples from patients carrying mutation(s) in the isocitrate dehydrogenase 1 (IDH1) gene, known to be associated with good prognoses, were excluded from this analysis. Of the remaining 339 IDH1 wild-type samples, raw Nanostring counts were log 2 transformed and the mean expression and standard deviation across all samples was adjusted to the same reference values applied to the training set of Example 2 above.

For classification, only expression values for the 30 classifier probes was considered and for each sample the Pearson correlation coefficient with respect to the each of the three Nanostring-specific centroids was determined. Samples were assigned to the subtype with the highest positive correlation coefficient. 42 (12.3%) samples did not show any positive correlation to any of the centroids and were labelled "Unclassified" (Table 7).

TABLE 7

Subtype assignments for the AvaGlio trial samples

| | Number of AvaGlio Samples |
|---|---|
| Mesenchymal | 141 |
| Proneural (PN) | 99 |
| Proliferative | 57 |
| Unclassified | 42 |

A comparison between the Phillips subtype classification based on the 30 classifier genes described above and the TCGA subtype classification (Verhaak et al. *Cancer Cell.* 17(1): 98-110, 2010) based on 95 classifier genes is shown below in Table 8.

TABLE 8

Comparison of subtype assignments based on Phillips and TCGA classifications

| | | Phillips | | | |
|---|---|---|---|---|---|
| | | Proneural | Mesenchymal | Proliferative | Unclassified |
| TCGA | Proneural | 70 | 1 | 13 | 8 |
| | Mesenchymal | 6 | 109 | 3 | 14 |
| | Classical | 12 | 24 | 33 | 10 |
| | Unclassified | 0 | 3 | 1 | 10 |
| | Neural | 11 | 4 | 7 | 0 |

Of the 99 patients classified as having a PN subtype of glioblastoma, as defined by Phillips et al., the selected baseline characteristics separated by treatment arm are shown below in Table 9.

TABLE 9

Selected baseline characteristics of PN subtype patients

| | | Proneural (IDH1 wild-type tumors) | |
|---|---|---|---|
| Patients, % | | RT/TMZ/PLB (n = 56) | RT/TMZ/BEV (n = 43) |
| Median age, years (range) | | 58.5 (21-78) | 59 (36-84) |
| Gender | Male | 68 | 54 |
| | Female | 32 | 42 |
| WHO PS | 0 | 52 | 30 |
| | 1-2 | 48 | 66 |
| RPA class - CRF | III | 12 | 7 |
| | IV | 64 | 60 |
| | V | 23 | 28 |
| MGMT status | Methylated | 27 | 37 |
| | Non-methylated | 54 | 40 |
| Surgical status | Biopsy | 7 | 9 |
| | Partial resection | 57 | 56 |
| | Complete resection | 36 | 30 |
| KPS | 50-80 | 36 | 42 |
| | 90-100 | 64 | 54 |
| MMSE score | <27 | 25 | 26 |
| | ≥27 | 75 | 65 |
| Corticosteroids | On | 54 | 49 |
| | Off | 46 | 46 |

To investigate how robust the classification of the AvaGlio samples into the three gene expression subtypes was, we also performed an unsupervised analysis (partitioning around medoids (Kaufman & Rousseeuw, *Clustering by Means of Medoids*. Reports of the Faculty of Mathematics and Informatics, Delft University. of Technology, 1987) using the same 30 classifier genes, sorting the samples into three clusters (k=3). Importantly, the nature of the clusters was not pre-specified, but was determined by the algorithm automatically. Samples with negative Silhouette width, indicating that their expression did not match the final cluster assignment, were labelled "Unclassified."

We observed very high concordance between the supervised and unsupervised analyses, e.g. the automatically determined sample clusters largely overlapped with the centroid-derived subtypes (Table 10).

TABLE 10

Supervised and unsupervised stratification of the AvaGlio samples

| | | Supervised Subtype | | | |
|---|---|---|---|---|---|
| | | Mes | PN | Prolif | Unclassified |
| PAM | Mes | 137 | 0 | 2 | 25 |
| | PN | 1 | 91 | 4 | 11 |
| | Prolif | 1 | 7 | 43 | 2 |
| | Unclassified | 2 | 1 | 8 | 4 |

Example 4. Patients Having Proneural (PN) Type Glioblastomas Showed Extension of Progression-Free Survival (PFS) and Overall Survival (OS) Following Bevacizumab Treatment in the AvaGlio Trial In the phase III AvaGlio trial, the addition of anti-VEGF antibody therapy in the treatment arm resulted in an overall increase in the median progression-free survival (PFS) by about 4.4 months compared to the placebo arm, but median overall survival (OS) was not significantly different between arms. We therefore determined whether any patients, defined using the Phillips classification by their tumor gene expression subtype of glioblastoma, derived an OS benefit from the addition of anti-VEGF therapy to treatment with RT and chemotherapy.

Upon stratification of both the PFS and OS data according to the subtype of glioblastoma as defined using the Phillips classification, we observed PFS and OS increases in the treatment arm of the AvaGlio trial compared to the placebo arm for patients having a glioblastoma of the PN subtype (n=99 patients, representing approximately 28.3% of all patients in the AvaGlio study).

Figure 2A:
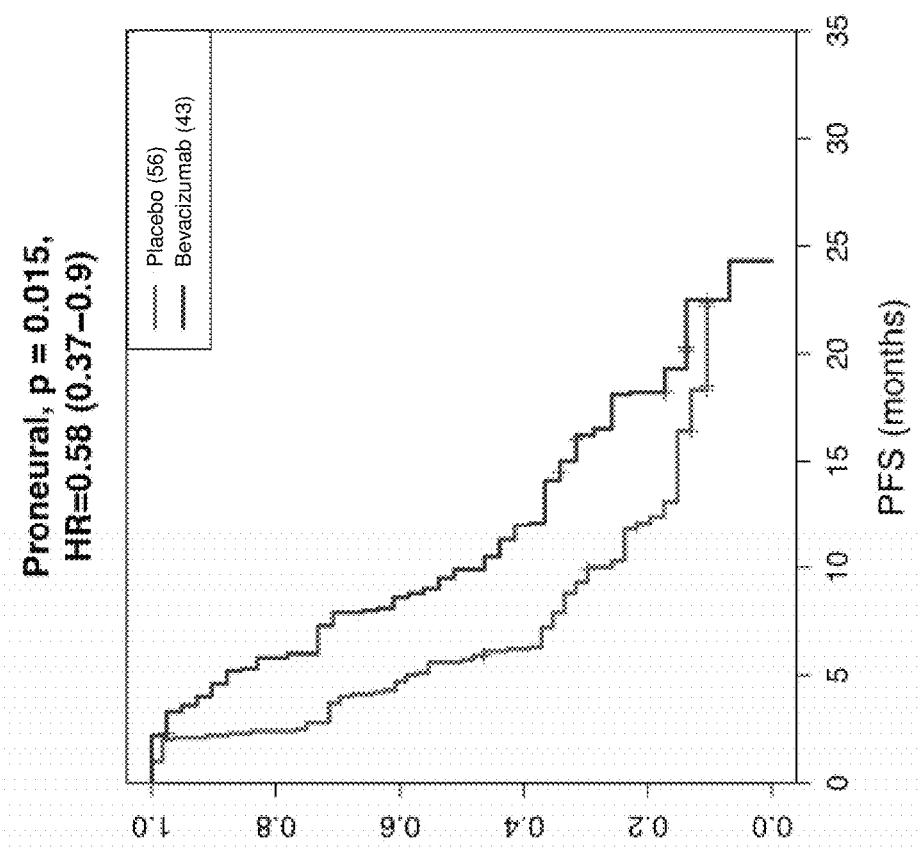
FIG. 2A is a graph showing the Kaplan Meier Curve for progression-free survival (PFS) of evaluated patients having glioblastoma of the proneural (PN) type, from the placebo and bevacizumab-treated arms of the Phase III AvaGlio trial, outlined in FIG. 1. n=99.
Figure 2B:
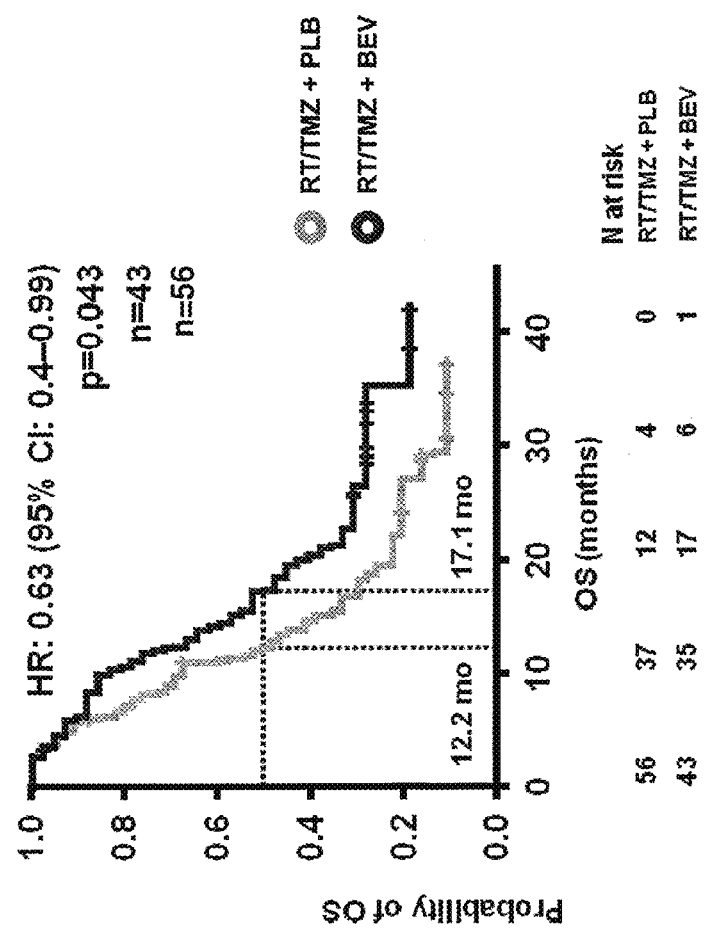
FIG. 2B is a graph showing the Kaplan Meier Curve for overall survival (OS) of evaluated patients having glioblastoma of the proneural (PN) type, from the placebo and bevacizumab-treated arms of the Phase III AvaGlio trial, outlined in FIG. 1. n=99.

With respect to PFS of the PN patients, which have the worst OS prognosis under standard of care, we observed extension of median PFS by about 4.3 months, with a hazard ratio (HR) equal to 0.58 (95% confidence interval (CI) =0.37-0.9; p=0.015) in the treatment arm relative to the placebo arm (see FIG. 2A). With respect to OS of the PN patients, we observed extension of median OS by about 4.9 months, with a HR equal to 0.63 (95% CI=0.4-0.99; p=0.043) in the treatment arm relative to the placebo arm (see FIG. 2B).

Figure 3:
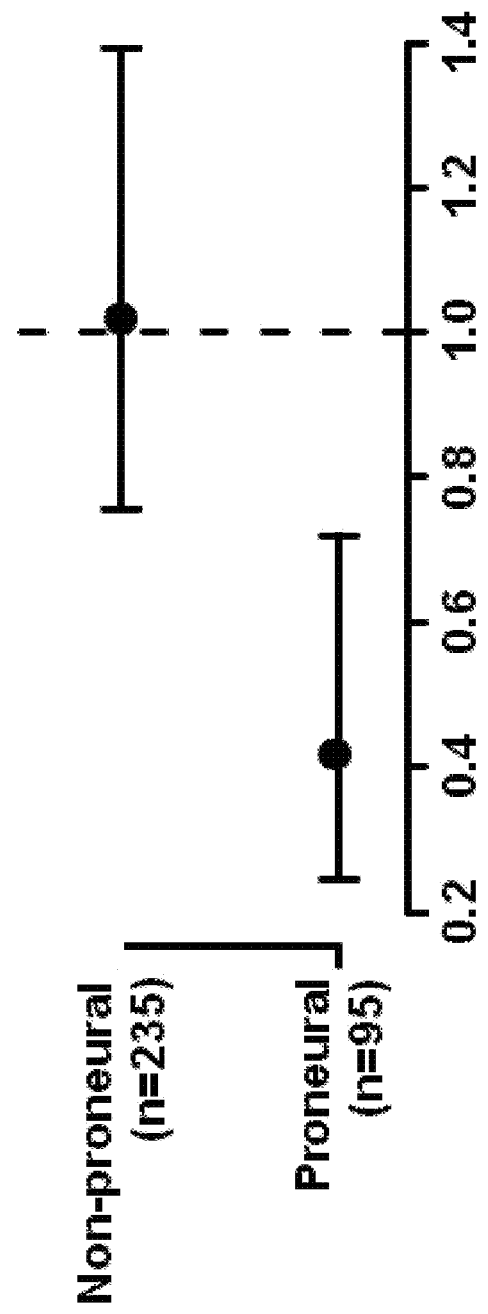
FIG. 3 is a graph showing OS of patients having PN (n=95) and non-PN (n=235) type glioblastoma from the treatment arm of the Phase III AvaGlio trial, adjusted for known clinical prognostic factors by multivariate analysis. Addition of bevacizumab to RT and chemotherapy treatment conferred a statistically significant benefit in extending OS for patients with IDH1 wild-type PN glioblastoma (HR: 0.42, 95% CI: 0.24-0.72, p=0.002—interaction between PN subtype and bevacizumab treatment: p=0.012). n=10 IDH1 mutation-positive patients and n=9 patients with missing covariate information were excluded from the multivariate Cox-proportional hazard analysis.
Figure 4A:
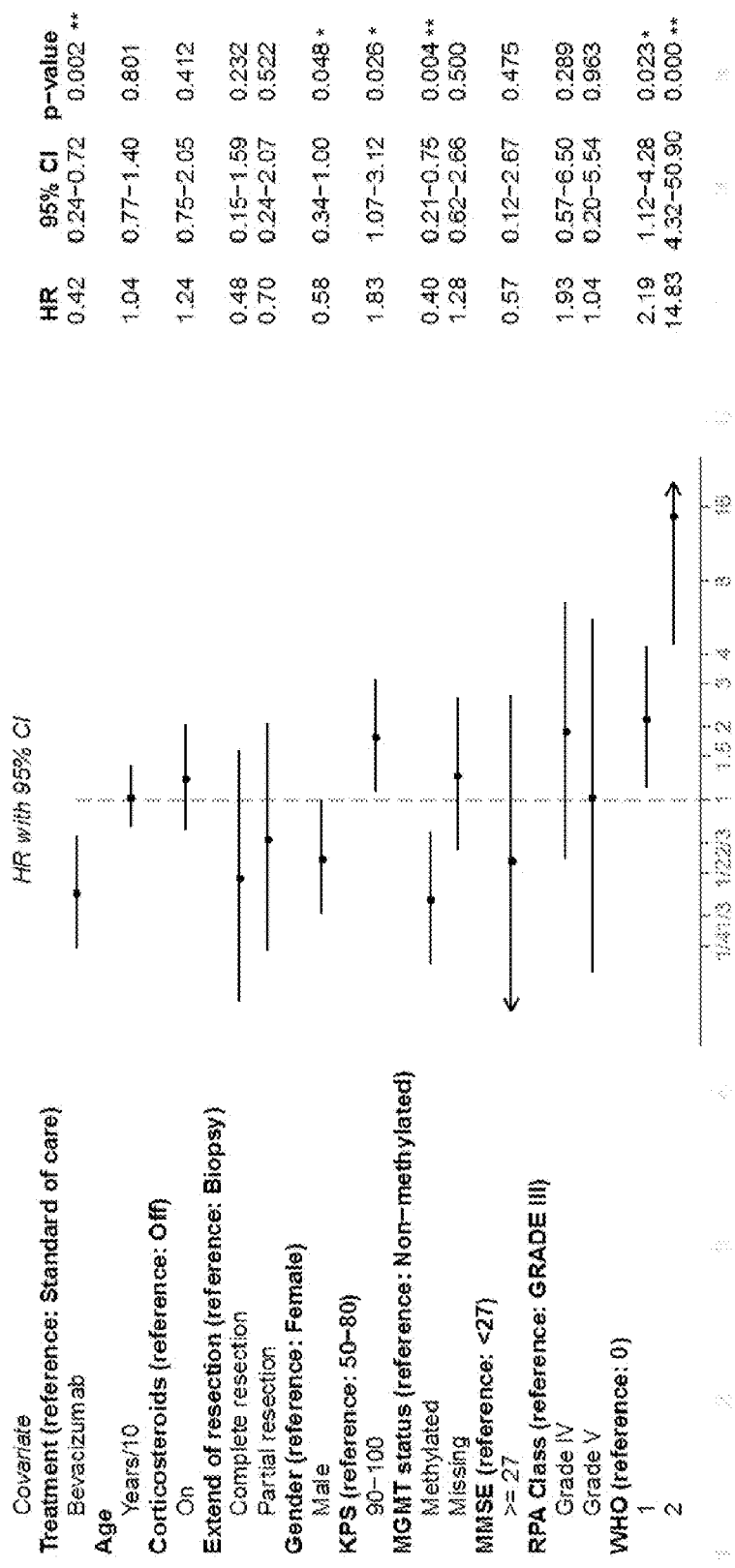
FIG. 4A is a graph showing significant OS benefit of bevacizumab-treated patients with Phillips-classified PN subtype glioblastoma when known prognostic covariates are considered. *p<0.5, **p<0.05.
Figure 4B:
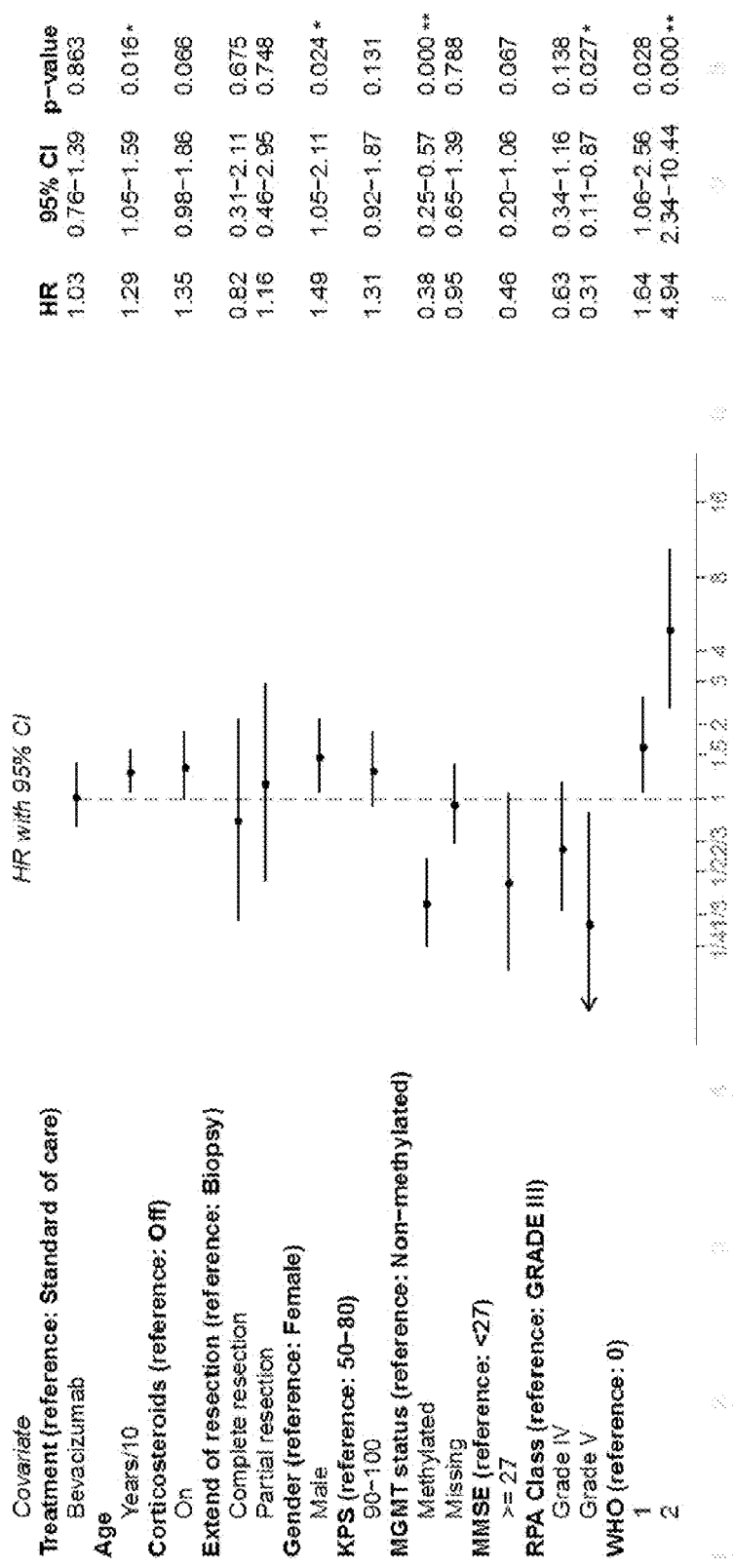
FIG. 4B is a graph showing that bevacizumab-treated patients with Phillips-classified non-PN subtype glioblastoma do not show significant OS benefit when known prognostic covariates are considered. *p<0.5, **p<0.05.

We also conducted a multivariate analysis of the effect of anti-VEGF therapy (e.g., anti-VEGF antibody therapy, e.g., bevacizumab therapy) in combination with RT and chemotherapy on OS in order to account for known clinical prognostic covariates (e.g., age, corticosteroids, extent of resection, gender, Karnofsky Performance Score (KPS), methylation status of O-6-methylguanine-DNA methyltransferase (MGMT) promoter, mini-mental state examination score (MMSE), recursive partitioning analysis (RPA) class, and WHO performance score). This analysis was performed using a multivariate Cox proportional hazard (PH) model fitted to OS for patients with PN and non-PN subtype glioblastoma tumors, as defined by Phillips. The multivariate Cox PH indicates that anti-VEGF therapy resulted in a significant OS benefit for patients having PN subtype glioblastoma, but not for patients having non-PN subtype glioblastoma (FIG. 3). Specifically, for patients having PN subtype glioblastoma, median OS in the treatment arm was 17.1 months compared to 12.2 months in the placebo arm, with a HR equal to 0.42 (95% CI=0.24-0.72; p=0.002) (FIG. 4A). For patients having non-PN subtype glioblastoma, HR was equal to 1.03 (95% CI=0.76-1.39; p=0.863) (FIG. 4B).

Figure 5A:
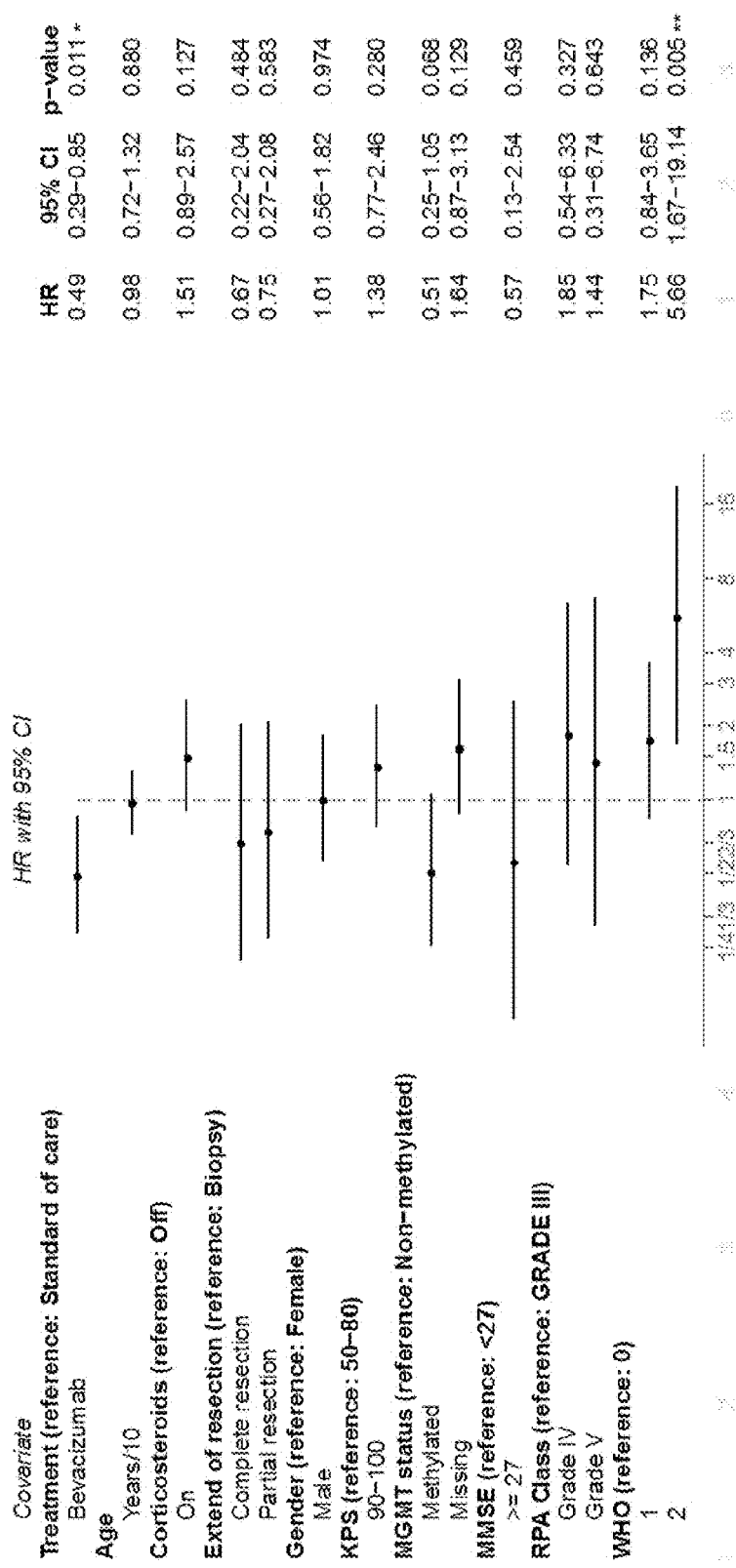
FIG. 5A is a graph showing significant OS benefit it of bevacizumab-treated patients with TCGA-classified PN subtype glioblastoma when known prognostic covariates are considered. *p<0.5, **p<0.05.
Figure 5B:
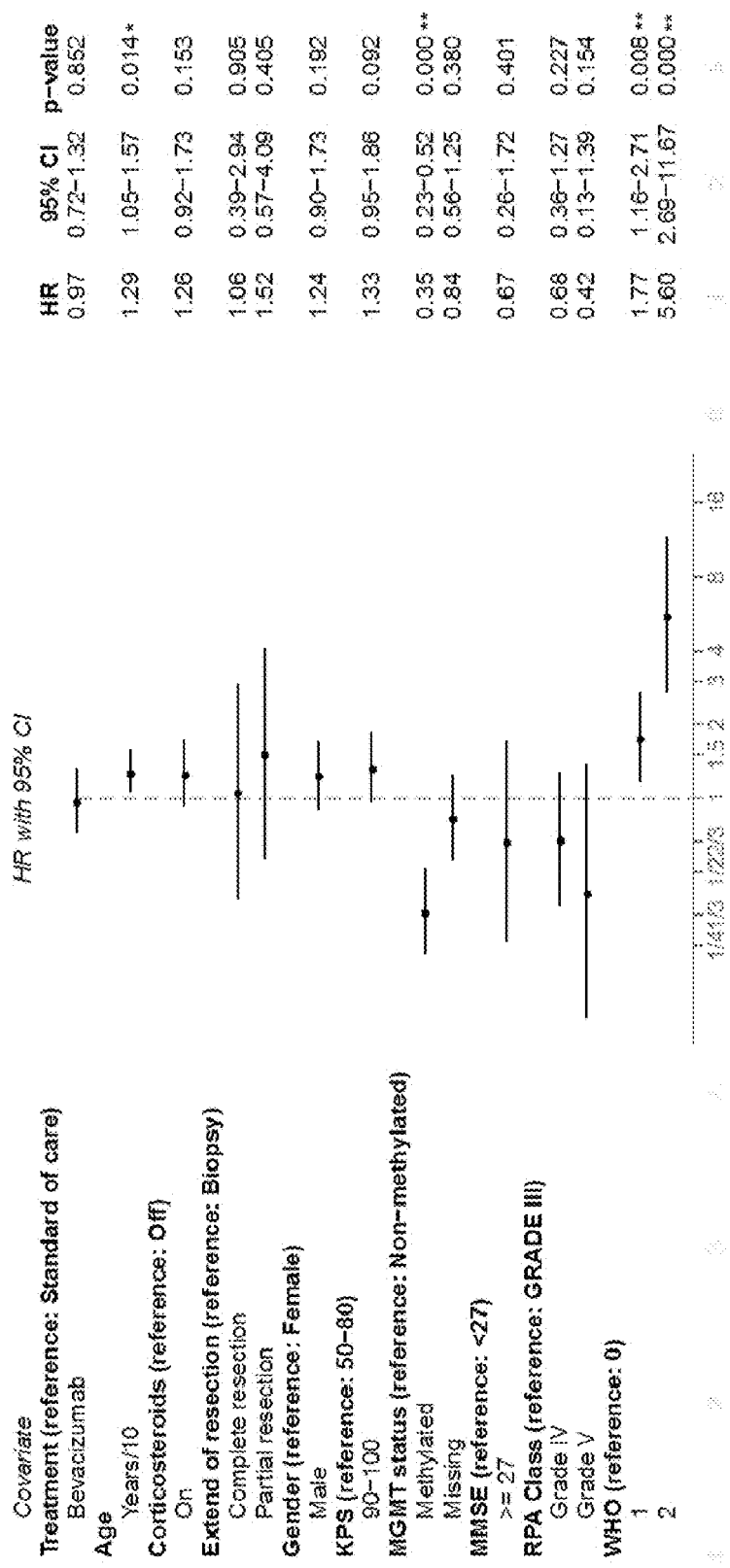
FIG. 5B is a graph showing that bevacizumab-treated patients with TCGA-classified non-PN subtype glioblastoma do not show significant OS benefit when known prognostic covariates are considered. *p<0.5, **p<0.05.

Multivariate analysis of the effect of anti-VEGF therapy (e.g., anti-VEGF antibody therapy, e.g., bevacizumab therapy) on OS for patients with PN and non-PN subtype glioblastoma classified by TCGA (Verhaak et al. *Cancer Cell.* 17(1): 98-110, 2010) also indicated significant OS benefit for patients having PN subtype glioblastoma (FIGS. 5A and 5B).

These data show that anti-VEGF antibody therapy (e.g., bevacizumab therapy) is associated with significant PFS and OS improvement (i.e., extension of PFS and OS time) for patients having glioblastoma of the PN type.

Although the foregoing invention has been described in some detail by way of illustration and example for purposes of clarity of understanding, the descriptions and examples should not be construed as limiting the scope of the invention. The disclosures of all patents, patent applications, scientific references, and Genbank Accession Nos. cited herein are expressly incorporated by reference in their entirety for all purposes as if each patent, patent application, scientific reference, and Genbank Accession No. were specifically and individually incorporated by reference.

What is claimed is:

1. A method of treating a patient diagnosed with a proneural subtype glioblastoma comprising administering to said patient a therapy comprising an effective amount of an anti-VEGF antibody, an effective amount of temozolomide (TMZ), and an effective amount of radiotherapy, wherein said anti-VEGF antibody comprises a variable heavy chain (VH) and a variable light chain (VL), wherein said VH comprises the amino acid sequence of SEQ ID NO: 2 and said VL comprises the amino acid sequence of SEQ ID NO: 1, and wherein said treatment prolongs said patient's median overall survival time as compared to a proneural subtype glioblastoma patient receiving TMZ without said anti-VEGF antibody, and wherein said patient is human.

2. The method of claim 1, wherein said patient has a WHO performance status of <2.

3. The method of claim 1, wherein the TMZ is administered at 150 mg/m$^2$.

4. The method of claim 1, wherein the TMZ is administered at 200 mg/m$^2$.

5. The method of claim 1, wherein the radiotherapy is administered at 2 Gy.

6. The method of claim 1, wherein said anti-VEGF antibody is bevacizumab.

7. The method of claim 1, wherein said effective amount of said anti-VEGF antibody is 10 mg/kg intravenously every two weeks.

8. The method of claim 1, wherein said effective amount of said anti-VEGF antibody is 15 mg/kg intravenously every three weeks.

9. The method of claim 1, wherein said effective amount of said anti-VEGF antibody is administered initially intravenously over 90 minutes, with subsequent infusions over 60 minutes and then 30 minutes.

10. The method of claim 1, wherein said anti-VEGF antibody is administered first to said patient at the first cycle.

11. The method of claim 9, wherein subsequence infusions of said anti-VEGF antibody are either prior to or after said temozolomide.

12. The method of claim 1, wherein said glioblastoma is a newly diagnosed glioblastoma.

13. The method of claim 1, wherein said anti-VEGF antibody is administered concurrently with TMZ.

14. The method of claim 1, wherein said median overall survival time is prolonged by about 4.9 months with a hazard ratio (HR) equal to 0.42.

15. The method of claim 1, wherein said median overall survival time is prolonged by about 4.9 months with a hazard ratio (HR) from about 0.24 to about 0.72.

16. The method of claim 14 or 15, wherein said patient is less than 65 years old.

17. The method of claim 14 or 15, wherein said patient is equal to or greater than 65 years old.

18. A method of treating a patient diagnosed with a proneural subtype glioblastoma comprising administering to said patient a therapy comprising an effective amount of bevacizumab, an effective amount of temozolomide (TMZ), and an effective amount of radiotherapy, wherein said treatment prolongs said patient's median overall survival time as compared to a proneural subtype glioblastoma patient receiving TMZ without said bevacizumab, and wherein said patient is human.

* * * * *

SEQUENCE LISTING

```
<160> NUMBER OF SEQ ID NOS: 2

<210> SEQ ID NO 1
<211> LENGTH: 108
<212> TYPE: PRT
<213> ORGANISM: Artificial Sequence
<220> FEATURE:
<223> OTHER INFORMATION: Synthetic Construct

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
                20                  25                  30

Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg
                100                 105

<210> SEQ ID NO 2
<211> LENGTH: 123
<212> TYPE: PRT
<213> ORGANISM: Artificial Sequence
<220> FEATURE:
<223> OTHER INFORMATION: Synthetic Construct

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
                20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
```

```
                65                  70                  75                  80
Leu Gln Met Asn Ser Leu Arg Ala Glu Asp Thr Ala Val Tyr Tyr Cys
                85                      90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120
```